(12) United States Patent
Koch et al.

(10) Patent No.: US 7,208,142 B2
(45) Date of Patent: Apr. 24, 2007

(54) INDANYLIDENE COMPOUNDS

(75) Inventors: Oskar Koch, Goettingen (DE); Erich Dilk, Holzminden (DE); Roland Langner, Bevern (DE); William Johncock, Höxter (DE)

(73) Assignee: Symrise GmbH & Co. KG (DE)

( * ) Notice: Subject to any disclaimer, the term of this patent is extended or adjusted under 35 U.S.C. 154(b) by 0 days.

(21) Appl. No.: 10/008,044

(22) Filed: Nov. 8, 2001

(65) Prior Publication Data

US 2002/0143203 A1    Oct. 3, 2002

(30) Foreign Application Priority Data

Nov. 10, 2000  (DE)  ................ 100 55 940

(51) Int. Cl.
*A61K 8/00*    (2006.01)
*A61K 8/18*    (2006.01)
*A61Q 17/04*   (2006.01)
*F21V 9/06*    (2006.01)
*C07D 319/00*  (2006.01)

(52) U.S. Cl. .................. 424/59; 424/401; 252/589; 549/359; 556/445; 556/447; 558/405

(58) Field of Classification Search ........... 252/589; 424/59, 401; 549/359; 556/445, 447; 558/405, 558/411
See application file for complete search history.

(56) References Cited

U.S. PATENT DOCUMENTS

| | | | |
|---|---|---|---|
| 4,514,231 A | 4/1985 | Kerner et al. | 106/445 |
| 5,403,944 A | 4/1995 | Frater et al. | 556/441 |
| 5,876,736 A * | 3/1999 | Cohen et al. | 424/401 |
| 5,965,066 A * | 10/1999 | Koch et al. | 252/589 |
| 6,153,175 A * | 11/2000 | Koch et al. | 424/59 |
| 6,416,746 B1 * | 7/2002 | Bringhen et al. | 424/59 |
| 6,600,589 B1 * | 7/2003 | Berneth et al. | 514/334 |
| 2003/0175616 A1 * | 9/2003 | Berneth et al. | 430/270.1 |

FOREIGN PATENT DOCUMENTS

| | | |
|---|---|---|
| DE | 199 19 630 | 11/2000 |
| DE | 10 016 669 A1 * | 10/2001 |
| WO | 00/14172 | 3/2000 |
| WO | WO 00/14172 | 3/2000 |

OTHER PUBLICATIONS

Ugo et al., "Novel Approach to the Ring-Opening of 4-Isoxazolines: One-Pot Synthesis of alpha, beta-Enones", Tetrahedron, vol. 48, No. 1, pp. 123-132 (Jan. 1992).*
Database CA 'Online! Chemical Abstracts Service, Columbus, Ohio, US: Chiacchio, Ugo et al.
"Novel approach to the ring-opening of 4-isoxazolines: one-pot synthesis of alpha.,.beta.-enones" retrieved from STN Database accession No. 116:128741 CA XP002199251 siehe RN: 139286-80-9 'Marker: 0055! Zusammenfassung & Tetrahedron (1992), 48(1), 128-32, (Jan. 1992).
Helv. Chim Acta, 159, (month unavailable) 1965, pp. 14761485, von F.-H. Marquardt, Friedel-Crafts-Reaktionen mit aromatischen Äthern, 1965- month unknown.
Int. J. of Cosmetic Science, 16, (month unavailable) 1994, B.L. Diffey, A method for broad Spectrum classification of sunscreens, pp. 47-52, month unknown.

* cited by examiner

*Primary Examiner*—Daniel S. Metzmaier
(74) *Attorney, Agent, or Firm*—Akerman Senterfitt

(57) ABSTRACT

Novel indanylidene compounds can be used as UV-A filters in cosmetic compositions for protecting skin and hair and for technical applications.

21 Claims, No Drawings

INDANYLIDENE COMPOUNDS

FIELD OF THE INVENTION

The invention relates to novel indanylidene compounds, to a process for their preparation and to their use as UVA filters.

BACKGROUND OF THE INVENTION

Indanylidene compounds which have UV-absorbing properties are already known from EP-A 823 418. However, the indanylidene compounds previously described in EP-A 823 418 have a photostability which is too low for the application.

SUMMARY OF THE INVENTION

Novel indanylidene compounds of the formula

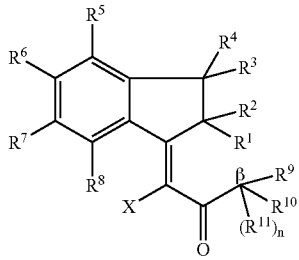

(I)

in which $R^1$ to $R^4$, independently of one another are hydrogen, $C_1$–$C_{20}$-alkyl or $C_5$–$C_{10}$-cycloalkyl, with the proviso that two substituents on adjacent carbon atoms can together also be an optionally substituted $C_1$–$C_4$-alkylene group;

may also, independently of one another, be $C_2$–$C_{20}$-alkyl, in which at least one methylene group may be replaced by oxygen, $C_3$–$C_{20}$-alkenyl, $C_3$–$C_{20}$alkynyl or a group S, where S may be a silane, an oligosiloxane or a polysiloxane group;

$R^5$ to $R^8$, independently of one another, are hydrogen, $C_1$–$C_{20}$-alkyl or $C_5$–$C_{10}$-cycloalkyl or $C_1$–$C_{20}$-alkoxy, $C_5$–$C_{10}$-cycloalkoxy, hydroxyl, acetoxy, acetamino, carboxyl, carbalkoxy or carbamoyl, additionally two substituents of $R^5$ to $R^8$ on adjacent carbon atoms can together form a 5–7-membered ring which contains up to three heteroatoms, where the ring atoms may be substituted by exocyclically double-bonded oxygen (keto group), also, in the case of alkoxy, may, independently of one another, be $C_2$–$C_{20}$-alkyl in which at least one methylene group may be replaced by oxygen, $C_3$–$C_{20}$-alkenyl, $C_3$–$C_{20}$-alkynyl or a group S, where S may be a silane, an oligosiloxane or a polysiloxane group;

X is cyano, $CON(R)_2$ or $CO_2R$, where R is hydrogen or $C_1$–$C_8$-alkyl;

n is 1 or 0;

$R^9$ to $R^{11}$, in cases where n=1, may be hydrogen, $C_1$–$C_{20}$-alkyl or $C_5$–$C_{10}$-cycloalkyl, aryl or heteroaryl, additionally two substituents of $R^9$ to $R^{11}$ can, together with the β-atom form a 3–7-membered ring which may contain up to three heteroatoms, also, in cases where n=0, $R^9$ and $R^{10}$, together with the β-atom, are an aryl or heteroaryl radical have been found.

DETAILED DESCRIPTION OF THE INVENTION

The present invention relates to novel indanylidene compounds of the formula

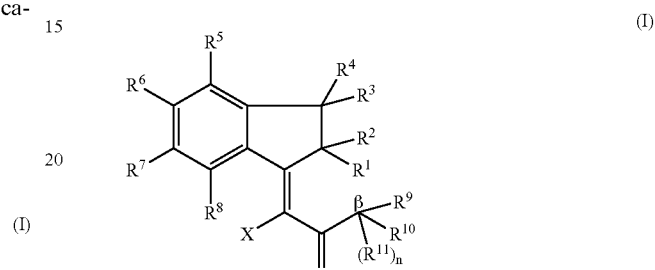

(I)

in which $R^1$ to $R^4$, independently of one another are hydrogen, $C_1$–$C_{20}$-alkyl or $C_5$–$C_{10}$-cycloalkyl, with the proviso that two substituents on adjacent carbon atoms can together also be an optionally substituted $C_1$–$C_4$-alkylene group;

may also, independently of one another, be $C_2$–$C_{20}$-alkyl, in which at least one methylene group may be replaced by oxygen, $C_3$–$C_{20}$-alkenyl, $C_3$–$C_{20}$alkinyl or a group S, where S may be a silane, an oligosiloxane or a polysiloxane group;

$R^5$ to $R^8$, independently of one another, are hydrogen, $C_1$–$C_{20}$-alkyl or $C_5$–$C_{10}$-cycloalkyl or $C_1$–$C_{20}$-alkoxy, $C_5$–$C_{10}$-cycloalkoxy, hydroxyl, acetoxy, acetamino, carboxyl, carbalkoxy or carbamoyl, additionally two substituents of $R^5$ to $R^8$ on adjacent carbon atoms can together form a 5–7-membered ring which contains up to three heteroatoms, in particular oxygen or nitrogen, where the ring atoms may be substituted by exocyclically double-bonded oxygen (keto group), also, in the case of alkoxy, may, independently of one another, be $C_2$–$C_{20}$-alkyl in which at least one methylene group may be replaced by oxygen, $C_3$–$C_{20}$-alkenyl, $C_3$–$C_{20}$-alkynyl or a group S, where S may be a silane, an oligosiloxane or a polysiloxane group;

X is cyano, $CON(R)_2$ or $CO_2R$, where R is hydrogen or $C_1$–$C_8$-alkyl;

n is 1 or 0;

$R^9$ to $R^{11}$, in cases where n=1, may be hydrogen, $C_1$–$C_{20}$-alkyl or $C_5$–$C_{10}$-cycloalkyl, aryl or heteroaryl, additionally two substituents of $R^9$ to $R^{11}$ can, together with the β-atom form a 3–7-membered ring which may contain up to three heteroatoms, in particular oxygen or nitrogen, also, in cases where n=0, $R^9$ and $R^{10}$, together with the β-atom, are an aryl or heteroaryl radical.

The novel indanylidene compounds represent a surprising selection from the indanylidene compounds known from EP-A 823 418. They have a significantly higher photostability than the compounds mentioned in EP-A 823 418 and higher compatibility with other UV filters, such as, for example, isooctyl p-methoxycinnamate.

Preference is given to indanylidene compounds of the formula

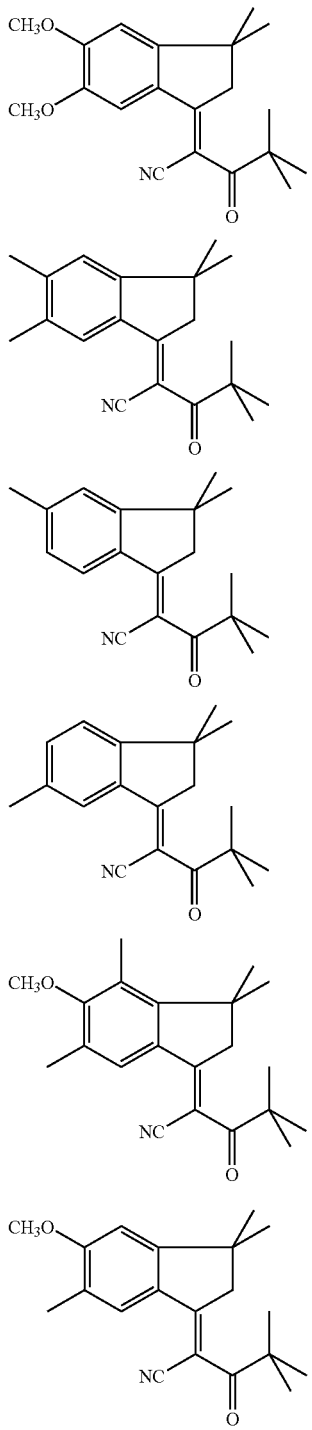

More preference is given to indanylidene compounds of the formula

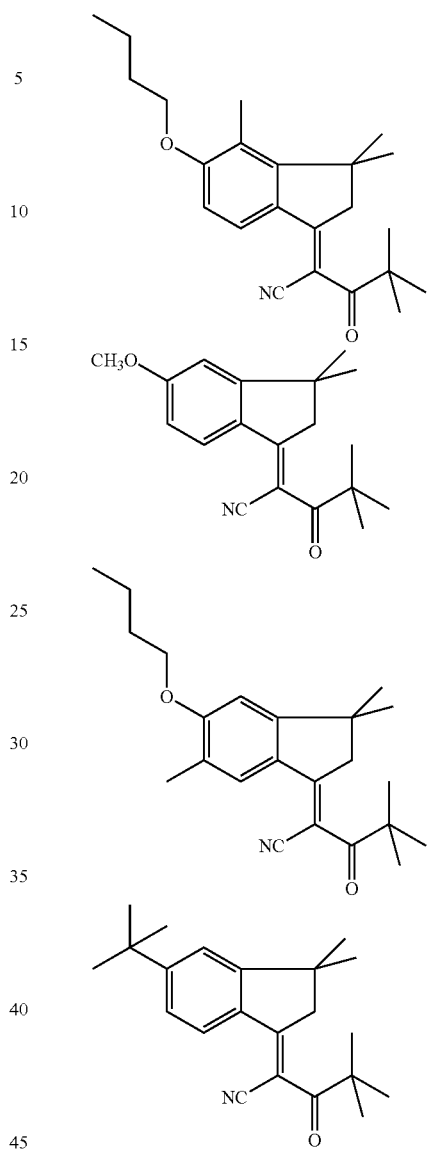

Specifically, the following preferred indanylidene compounds may be mentioned:

2-(5,6-Dimethoxy-3,3-dimethyl-1-indanylidene)-4,4-dimethyl-3-oxo-pentanonitrile, 2-(5-methoxy-3,3,4,6-tetramethyl-1-indanylidene)-4,4-dimethyl-3-oxo-pentanonitrile, 2-(3,3,5,6-tetramethyl-1-indanylidene)-4,4-dimethyl-3-oxo-pentanonitrile, 2-(3,3,6-trimethyl-1-indanylidene)-4,4-dimethyl-3-oxo-pentanonitrile, 2-(5,6-ethylenedioxo-3,3-dimethyl-1-indanylidene)-4,4-dimethyl-3-oxo-pentanonitrile, 2-(5-methoxy-3,3,6-trimethyl-1-indanylidene)-4,4-dimethyl-3-oxo-pentanonitrile, 2-[(5-methoxy-3,3-dimethyl-(2-methyl-3-(1,3,3,3-tetramethyl-1-(trimethyl-silyloxy)-disiloxanyl)-propyl)-indanylidene)]-4,4-dimethyl-3-oxo-pentanonitrile and 2-(6-acetoxy-3,3-dimethyl-5-methoxy-1-indanylidene)-4,4-dimethyl-3-oxo-pentanonitrile.

The indanylidene compounds according to the present invention can be prepared by (Knoevenagel) condensation of compounds of the formula

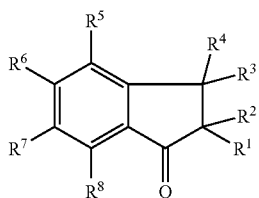

(II)

where
R¹ to R⁸ have the meanings given above, with compounds of the formula

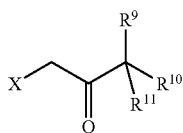

(III)

where
R⁹ to R¹¹ and X have the meanings given above.

The indanones used here can be prepared by Friedel-Crafts Reactions of (substituted) acrylic esters with (substituted) aromatics or, in the case of hydroxyl substituents, by Fries rearrangement of corresponding phenyl esters (F.-H. Marquardt, Helv. Chim. Acta 159, 1476 (1965)).

The preparation of the indanylidene compounds according to the present invention can, for example, be carried out as follows:

The above-mentioned indanones are condensed with equimolar amounts of pivaloylacetonitrile with the catalysis of ammonium acetate according to the conditions of a Knoevenagel condensation.

The preparation can be illustrated by the reaction scheme below:

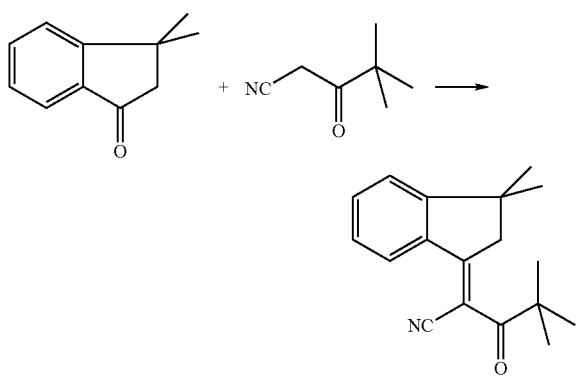

The indanylidene compounds according to the present invention can be used as UV absorbers, e.g. in cosmetic compositions, in particular for protecting against acute skin damage (sunburn) and also chronic skin damage (premature skin aging), particularly in sunscreen compositions, daily care products and hair care products, but also for improving the photostability of technical products, such as paints, surface coatings, plastics, textiles, packaging materials and rubbers.

The indanylidene compounds according to the present invention can be used individually or in a mixture in the corresponding preparations; it is also possible to use them in combination with UV absorbers of other classes of substance, and also with the latter in any desired mixtures with one another. For example, the following UV absorbers may be mentioned:
p-aminobenzoic acid
ethyl p-aminobenzoate (25 mol) ethoxylated
2-ethylhexyl p-dimethylaminobenoate
ethyl p-aminobenzoate (2 mol) N-propoxylated
glycerol p-aminobenzoate
homomethyl salicylate (homosalate) (Neo Heliopan®HMS)
ethylhexyl salicylate (Neo Heliopan®OS)
triethanolamine salicylate
4-isopropylbenzyl salicylate
menthyl anthranilate (Neo Heliopan®MA)
ethyl diisopropylcinnamate
2-ethylhexyl p-methoxycinnamate (Neo Heliopan®AV)
methyl diisopropylcinnamate
isoamyl p-methoxycinnamate (Neo Heliopan®E 1000)
p-methoxycinnamate acid diethanolamine salt
isopropyl p-methoxycinnamate
2-ethylhexyl 2-cyano-3,3-diphenyl acrylate (Neo Heliopan®303)
ethyl 2-cyano-3,3'-diphenyl acrylate
2-phenylbenzimidazolesulfonic acid and salts (Neo Heliopan®hydro)
3-(4'-trimethylammonium)-benzylidene-bornan-2-one methylsulfate
terephthalylidene-dibornanesulfonic acid and salts (Mexoryl®SX)
4-t-butyl-4'-methoxy-dibenzoylmethane (Avobenzone)/(Neo Heliopan®357)
β-imidazole-4(5)-acrylic acid (Urocanic acid)
2-hydroxy-4-methoxybenzophenone (Neo Heliopan®BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methylbenzophenone
3-(4'-sulfo)benzylidene-bornan-2-one and salts
3-(4'-methylbenzylidene)-d,l-camphor (Neo Heliopan®MBC)
3-benzylidene-d,l-camphor
4-isopropyidibenzoylmethane
2,4,6-trianilino-(p-carbo-2'-ethylhexyl-1'-oxy)-1,3,5-triazine
phenylene-bis-benzimidazyl-tetrasulfonic acid disodium salt (Neo Heliopan®AP)
2,2'-(1,4-phenylene)-bis-(1H-benzimidazole-4,6-disulfonic acid), monosodium salt
N-[(2 and 4)-[2-(oxoborn-3-ylidene)methyl]benzyl]-acrylamide-polymer
phenol, 2-(2H-benzotriazol-2-yl)-4-methyl-6-(2-methyl-3 (1,3,3,3-tetramethyl-1-(trimethylsilyl)-oxy)-disiloxanyl)-propyl), (Mexoryl®XL)
bis-(2-ethylhexyl) 4,4'-[(6-[4-(1,1-dimethyl)-aminocarbonyl)-phenylamino]-1,3,5-triazine-2,4-diyl)diimino]-bis-(benzoate) (Uvasorb®HEB)
2,2'-methylene-bis-(6-(2 H-benztriazol-2-yl)-4-1,1,3,3-tetramethyl butyl)-phenol), (Tinosorb®M)
2,4-bis-[4-(2-ethylhexyloxy)-2-hydroxyphenyl]-1,3,5-triazine
benzylidene malonate-polysiloxane (Parsol®SLX)

glycerylethyl hexanoate-dimethoxycinnamate
disodium 2,2'-dihydroxy-4,4'-dimethoxy-5,5'-disulfo-benzophenone
dipropylene glycol salicylate
sodium hydroxymethoxybenzophenonesulfonate
tris (2-ethylhexyl) 4,4',4-(1,3,5-triazine-2,4,6-triyltriimino)-tris-benzoate (Uvinul®T150)
2,4-bis-[{(4-(2-ethyl-hexyloxy)-2-hydroxy}-phenyl]-6-(4-methoxyphenyl)-1,3,5-triazine, (Tinosorb®S)
2,4-bis-[{(4-(3-sulfonato)-2-hydroxy-propyloxy)-2-hydroxy}-phenyl]-6-(4-methoxyphenyl)-1,3,5-triazine sodium salt
2,4-bis-[{(3-(2-propyloxy)-2-hydroxy-propyloxy)-2-hydroxy}-phenyl]-6-(4-methoxy-phenyl)-1,3,5-triazine
2,4-bis-[{4-(2-ethyl-hexyloxy)-2-hydroxy}-phenyl]-6-[4-(2-methoxyethyl-carbonyl)-phenylamino]-1,3,5-triazine
2,4-bis-[{4-(3-(2-propyloxy)-2-hydroxy-propyloxy)-2-hydroxy}-phenyl]-6-[4-(2-ethylcarboxyl)-phenylamino]-1,3,5-triazine
2,4-bis-[{4-(2-ethyl-hexyloxy)-2-hydroxy}-phenyl]-6-(1-methyl-pyrrol-2-yl-)-1,3,5-triazine
2,4-bis-[{4-tris-(trimethylsiloxy-silylpropyloxy)-2-hydroxy}-phenyl]-6-(4-methoxyphenyl)-1,3,5-triazine
2,4-bis-[{4-(2"-methylpropenyloxy)-2-hydroxy}-phenyl]-6-(4-methoxyphenyl)-1,3,5-triazine
2,4-bis-[{4-(1',1',1',3'5',5',5'-heptamethylsiloxy-2"-methyl-propyloxy)-2-hydroxy}-phenyl]-6-(4-methoxyphenyl)-1,3,5-triazine Particularly suitable UV absorbers are:
p-aminobenzoic acid
3-(4'-trimethylammonium)-benzylidene-bornan-2-one methylsulfate
homomethyl salicylate (Neo Heliopan®HMS)
2-hydroxy-4-methoxy-benzophenone (Neo Heliopan®BB)
2-phenylbenzimidazolesulfonic acid (Neo Heliopan®Hydro)
terephthalylidenedibornanesulfonic acid and salts (Mexoryl®SX)
4-tert-butyl-4'-methoxyd ibenzoylmethane (Neo Heliopan®357)
3-(4'-sulfo)benzylidene-bornan-2-one and salts
2-ethylhexyl 2-cyano-3,3-diphenylacrylate (Neo Heliopan®303)
N-[(2 and 4)-[2-(oxoborn-3-ylidene)methyl]benzyl]-acrylamide polymer
2-ethylhexyl p-methoxycinnamate (Neo Heliopan®AV)
ethyl p-aminobenzoate (25 mol) ethoxylated
isoamyl p-methoxycinnamate (Neo Heliopan®E1000)
2,4,6-trianilino-(p-carbo-2'-ethylhexyl-1'-oxy)-1,3,5-triazine (Uvinul®T150)
phenol, 2-(2H-benzotriazol-2-yl)-4-methyl-6-(2-methyl-3 (1,3,3,3-tetramethyl-1-(trimethylsilyl)-oxy)-disiloxanyl)-propyl), (Mexoryl®XL)
bis-(2-ethylhexyl) 4,4'-[(6-[4-(1,1-dimethyl)-aminocarbonyl)-phenylamino]-1,3,5-triazine-2,4-diyl)-diimino]-bis-(benzoate), (UvasorbHEB)
3-(4'-methylbenzylidene)-d,l-camphor (Neo Helipan®MBC)
3-benzylidenecamphor
2-ethylhexyl salicylate (Neo Heliopan®OS)
2-ethylhexyl 4-dimethylaminobenzoate (Padimate O)
hydroxy-4-methoxybenzophenone-5-sulfonic acid and Na salt
2,2'-methylene-bis-(6-(2H-benztriazol-2-yl)-4-1,1,3,3-tetramethylbutyl)-phenol), (Tinosorb®M)
phenylene-bis-benzimidazyltetrasulfonic acid disodium salt (Neo Heliopan®AP)
2,4-bis-[{(4-(2-ethyl-hexyloxy)-2-hydroxy}-phenyl]-6-(4-methoxyphenyl)-1,3,5-triazine, (Tinosorb®S)
benzylidene malonate-polysiloxane (Parsol®SLX)
menthyl anthranilate (Neo Heliopan®MA)

It may also be advantageous to use polymer-bonded or polymeric UV absorbers in preparations according to the present invention, in particular those described in WO-A-92/20690. The combination of the indanylidene compounds according to the present invention with finely divided inorganic and organic pigments, such as, for example, titanium dioxide, zinc oxide and iron oxide and Tinosorb®M, in sunscreen and daily care products with UV protection is likewise possible.

The list of UV filters given which can be used for the purposes of the present invention is not of course intended to be limiting.

The total amount of all (mono- and polysulfonated) water-soluble UV filter substances in the finished cosmetic or dermatological preparations, for example of phenylene-bis-benzimidazyl-tetrasulfonic acid disodium salt or salts thereof and/or the corresponding disulfonic acid or salts thereof and/or 2-phenylbenzimidazole-5-sulfonic acid and salts thereof and/or 2-hydroxy-4-methoxybenzophenone-5-sulfonic acid and salts thereof and/or 4-(2-oxo-3-bornylidenemethyl)-benzenesulfonic acid and salts thereof and/or 2-methyl-5-(2-oxo-3-bornylidene-methyl)-benzenesulfonic acid and salts thereof and/or benzene-1,4-di-(2-oxo-3-bornylidenemethyl)-10-sulfonic acid and salts thereof, is advantageously chosen from the range from 0.1 to 10.0% by weight, preferably 0.5 to 6.0% by weight, based on the total weight of the preparations, if the presence of these substances is desired.

The total amount of oil-soluble UV filter substances in the finished cosmetic or dermatological preparations, for example of tris(2-ethylhexyl) 4,4',4"-(1,3,5-triazine-2,4,6-triyltriimino)-tris-benzoate and/or 4-tert-butyl-4'-methoxy-dibenzoylmethane and/or 4-methylbenzylidenecamphor and/or octyidimethyl-p-aminobenzoic acid and/or Mexoryl®XL and/or Uvasorb®HEB and/or Tinosorb®S and/or benzophenone-3 and/or Parsol®SLX and/or Neo Heliopan®MA is advantageously chosen from the range from 0.1 to 10.0% by weight, preferably 0.5 to 6.0% by weight, based on the total weight of the preparations, if the presence of these substances is desired.

The total amount of 2-ethylhexyl p-methoxycinnamate and/or isoamyl p-methoxycinnamate in the finished cosmetic or dermatological preparations is advantageously chosen from the range from 0.1 to 15.0% by weight, preferably 0.5 to 7.5% by weight, based on the total weight of the preparations, if the presence of these substances is desired.

The total amount of ethyihexyl 2-cyano-3,3-diphenylacrylate in the finished cosmetic or dermatological preparations is, if the presence of this substance is desired, advantageously chosen from the range from 0.1 to 15.0%, preferably 0.5 to 10.0% by weight, based on the total weight of the preparations.

The total amount of one or more salicylic acid derivatives in the finished cosmetic or dermatological preparations is advantageously chosen from the range from 0.1 to 15.0% by weight, preferably 0.5 to 10.0% by weight, based on the total weight of the preparations. If ethylhexyl salicylate is chosen, it is advantageous to choose its total amount from the range from 0.1 to 5.0% by weight. If homomenthyl salicylate is chosen, it is advantageous to choose its total amount from range from 0.1 to 10.0% by weight.

The indanylidene compounds according to the present invention are also suitable to a particular degree for photostabilizing UV absorbers with low UV photostability. The photostabilization of the very photo-unstable compounds of the dibenzoylmethane, e.g. tert-butyl-4'-methoxydibenzoylmethane, is particularly successful.

A further photostable UV filter combination is achieved using 0.1 to 10% by weight, preferably 1 to 10% by weight, of ethylhexyl p-methoxycinnamate or isoamyl p-methoxy cinnamate with 0.1 to 10% by weight, preferably 1 to 6% by weight, of the compound of the formula 1, preferably in the ratio 1:1.

The combinations of p-methoxycinnamic esters and dibenzoylmethane derivatives and compounds of the formula I can be formulated to be photostable by using, for example, 0.1 to 5% by weight, preferably 1 to 3% by weight, of 4-tert-butyl-4'-methoxydibenzoyl-methane, 0.1 to 10% by weight, preferably 1 to 7.5% by weight of ethylhexyl p-methoxycinnamate or isoamyl p-methoxycinnamate and at least 0.2% by weight, preferably 1 to 6% by weight, of the compounds of the formula 1, preferably in the ratio 1 part of dibenzoylmethane derivative, 2 parts p-methoxycinnamic ester and 2 parts of the indanylidene compounds according to the invention.

In addition, it is advantageous to add one or more very photostable UV absorbers to this three-way combination, such as, for example, methylbenzylidenecamphor, 2-ethylhexyl 2-cyano-3,3'-diphenylacrylate, octyltriazone, Uvasorb®HEB, Tinosor®S, Tinosor®M, ethylhexyl salicylate, homomenthyl salicylate, and phenylenebisimidazolesulfonic acid or phenylene-bis-benzimidazole-tetrasulfonic acid disodium salt, Mexoryl®SX, Mexoryl®XL or Parsol®SLX.

In addition, in cosmetic preparations, a synergistic increase in the sun protection factor is surprisingly achieved using indanylidene derivatives of the formula I in combination with other UV filters. Examples of a synergistic increase in the sun protection factor are cosmetic emulsions which comprise both a compound of the formula I and also ethylhexyl methoxycinnamate or octocrylene, or a combination of a compound of the formula I with ethylhexyl methoxycinnamate and 2-phenylbenzimidazolesulfonic acid, or ethylhexyl methoxycinnamate and methylbenzylidenecamphor, or ethylhexyl methoxycinnamate and 4-t-butyl-4'-methoxydibenzoylmethane, or Neo Heliopan®AP and ethylhexyl methoxycinnamate, or a combination of a compound of the formula I with octocrylene, methylbenzylidenecamphor and zinc oxide. Combinations of a compound of the formula I with dibenzoylmethanes, methylbenzylidene-camphor, 2-phenylbenzimidazolesulfonic acid, Neo Heliopan®AP, Mexoryl®SX, Mexoryl®XL, Parsol®SLX, Tinosorb®S, Tinosor®M, Uvinul®T150, Uvasorb®HEB, and microfine pigments, zinc oxide and titanium oxide, also have synergistic increases in the sun protection factors. Such UV filter combinations are listed by way, of example, and are not to be understood as being limited to the above-mentioned combinations. Thus, it is possible to use combinations of all UV absorbers already mentioned as particularly suitable on pages 8/9, and UV filters approved in the subsequent publications with compounds of the formula I or the above-mentioned combinations, individually or in any desired mixtures.

USA: Food and Drug Administration (FDA). Publication in monograph for Sunscreen Drug Products for Over-The-Counter Human Use.

Europe: EC Directive 76/768 of the Council for adapting the legal provisions of the member states regarding cosmetic compositions to technical progress. Publications in the Official Journal of European Communities.

Japan: Publication of the Cosmetics Directive of the Ministry of Health and Welfare (MHW).

Germany: Publication in the Verordnung über kosmetische Mittel [Directive concerning cosmetic compositions] according to the Lebensmittel- und Bedarfsgegenstände-Gesetz (LMBG) [Act relating to Foods and Commodities].

Australia: Registration by Therapeutic Goods Administration (TGA) and publication in the Australian Register of Therapeutic Goods (ARTG).

These combinations usually achieve a synergistic increase in the UV sun protection factor.

The combination of compounds of the formula I with UV-A absorbers, particularly UV-A-II absorbers, gives broad protection against UV-A radiation (320–400 nm). In particular, a combination of compounds of the formula I with Neo Heliopan®AP (UV-A-II absorber) is to be mentioned for broad UV-A protection performance. Further, UV-A filters which are used in combination with compounds of the formula I alone or in combination of compounds of the formula I and Neo Heliopan®AP are Mexoryl®SX, Mexoryl®XL, Tinosor®M Tinosorb®S, benzophenone-3, benzophenone-4, Neo Heliopan®357, Neo Heliopan®MA.

For optimum broad-band protection against UV-A and UV-B radiation, the above-mentioned combinations are to be combined with all UV-B filters and mixtures of these filters (cf. list on pages 6–9). Preferably suitable are Neo Heliopan®AV, Neo Heliopan®E1000, Neo Heliopan®Hydro, Neo Heliopan®MBC, Neo Heliopan®303, Neo Heliopan®OS, Neo Heliopan®HMS, Uvinul®T150, Uvasorb®HEB, ethylhexyl dimethylaminobenzoate.

Combining compounds of the formula I with Neo Heliopan®AP and a UV-B filter, e.g. ethylhexyl methoxycinnamate or UV-B filter mixtures, and coated or uncoated finely disperse metal oxides, such as, for example, zinc oxide, titanium dioxide, achieves UV broad-band protection performance with a critical wavelength $\lambda_{crit}$ of >380 nm (cf. Diffey in Int. J. Cosm. Science 16, 47 (1994)).

Furthermore, the indanylidene compounds according to the present invention can be combined alone or with other UV absorbers used for the protection of technical products. Examples of such UV absorbers are compounds from the series of benzotriazoles, benzophenones, triazines, cinnamonic esters and oxalanilides.

The indanylidene compounds according to the present invention are crystalline and have to be dissolved sufficiently in cosmetic preparations to avoid the problem of recrystallization following a prolonged storage period. A sufficient amount of the oil components customarily used in cosmetic preparations, liquid oil-soluble UV absorbers or alcohols, e.g. ethanol, isopropanol or 1-butanol, is necessary to avoid recrystallization. More preference is given to the use of the following oil components and/or UV absorbers for achieving adequate solubility of combinations of the indanylidene compounds according to the present invention: ethylhexylmethoxycinnamate, isoamyl methoxycinnamate, octocrylene, ethylhexyl salicylate, homosalate, menthyl anthranilate, padimate O, diisopropyl adipate, $C_{12-15}$-alkyl benzoate (Witconol TN), butylene glycol dicaprylate/dicaprate (Miglyol 8810), cocoglycerides (Myritol 331), caprylic/capric triglycerides (Miglyol 812), cetearyl isononanate (Cetiol SN), PVP/hexadecene copolymer (Unimer U151), adipic acid/diethylene glycol/isononanoic acid copolymer (Lexorez 100), propylene glycol dicaprylate/ dicaprate (Myritol PC), hexyl laurate (Cetiol A), dicapryl ether (Cetiol OE), diethylhexyl naphthalate (Hallbrite®TQ), butyloctyl salicylate (Hallbrite®BHB), dibutyl adipate (Cetiol B), triethyl citrate (hydagen CAT), propylene glycol dibenzoate (Finsolv PG 22), tributyl citrate, dioctyl malate (Ceraphyl 45), dipropylen glycol dibenzoate (Benzoflex 245), acetyltributyl citrate (Citroflex A-4), acetyltriethyl citrate (Citroflex A-2). The list of the oils which can be used for the purposes of the present invention is not of course intended to be limiting.

The use amount of all oil components in cosmetic emulsions with compounds of the formula I is 0.5 to 30% by weight, preferably 2 to 15% by weight. All said oil components and liquid oil-soluble UV filters are excellent solvents for all crystalline oil-soluble UV absorbers.

It is a serious drawback if UV absorbers leave behind marks which cannot be washed out of items of clothing. In particular, it is known that the UV-A absorber tert-butyl-methoxydibenzoylmethane produces marks on textiles which cannot be washed out. The indanylidene compounds according to the present invention do not have this drawback since a mark formed on textiles can be very readily washed out.

Sunscreen products should be water-resistant in order that sufficient UV protection is ensured for the user, in particular children, while swimming or bathing. Combinations of the indanylidene compounds according to the present invention satisfy these requirements to a particularly good degree. In an O/W emulsion containing 3% by weight of a combination of the indanylidene compounds according to the present invention, 97% substantivity of the UV absorber was measured following washing, and in a W/O emulsion, 95%. Furthermore, the water resistance of sun protection products containing water-soluble, mono- or polysulfonated UV filters, such as, for example, Neo Heliopan®AP, Mexoryl®SX, benzophenone-4, Neo Heliopan®Hydro and the oil-soluble UV absorbers listed on pages 6–9 can be significantly increased as a result of combination with compounds of the formula I.

It may also be of considerable advantage to combine the UV absorbers mentioned according to the present invention with chelating substances, as are listed, for example, in EP-A 496 434, EP-A 313 305 and WO-94/04128, or with polyaspartic acid and ethylenediamine-tetramethyl-phosphonic acid salts.

Cosmetic and dermatological formulations for the purposes of the present invention comprise one or more customary UV-A, UV-B and/or broad-band filters as individual substances or in any mixtures with one another, in the lipid phase and/or in the aqueous phase. They are satisfactory products in every respect which are surprisingly characterized by high UV-A protection performance and high sun protection factor.

The present invention further provides for the use of the UV absorbers according to the present invention in combination with conventional UV absorbers for enhancing the protection against harmful UV radiation beyond the extent of the protection achieved using the same amounts of conventional or of UV filters according to the present invention on their own (synergistic effect).

The total amount of UV filter substances (UV-A, UV-B and/or broad-band filters) in the finished cosmetic or dermatological preparations, whether as individual substance or in any mixtures with one another, is advantageously chosen from the range from 0.1 to 30% by weight, preferably 0.1 to 10.0% by weight, more preferably 0.5 to 5.0% by weight, based on the total weight of the preparations.

In addition, cosmetic and dermatological preparations according to the present invention advantageously, but not obligatorily, comprise inorganic pigments based on finely disperse metal oxides and/or other metal compounds which are insoluble or sparingly soluble in water, in particular the oxides of titanium ($TiO_2$), zinc (ZnO), iron (e.g. $Fe_2O_3$), zirconium ($ZrO_2$), silicon ($SiO_2$), manganese (e.g. MnO), aluminum $Al_2O_3$), cerium (e.g. $Ce_2O_3$), mixed oxides of the corresponding metals, and mixtures of such oxides. These pigments are X-ray-amorphous or non-X-ray-amorphous. More preference is given to pigments based on $TiO_2$. X-ray-amorphous oxide pigments are metal oxides or semi-metal oxides which reveal no or no recognizable crystalline structure in X-ray diffraction experiments. Such pigments are often obtainable by flame reaction, for example by reacting a metal or semi-metal halide with hydrogen and air (or pure oxygen) in a flame.

In cosmetic, dermatological or pharmaceutical formulations, X-ray-amorphous oxide pigments are used as thickeners and thixotropic agents, flow auxiliaries for emulsion and dispersion stabilization and as carrier substance (for example for increasing the volume of finely divided powders). X-ray-amorphous oxide pigments which are known and often used in cosmetic or dermatological galenics are, for example, high-purity silicon oxide. Preference is given to high-purity, X-ray-amorphous silicon dioxide pigments with a particle size in the range from 5 to 40 nm and an active surface area (BET) in the range from 50 to 400 $m^2/g$, preferably 150 to 300 $m^2/g$, where the particles are to be regarded as spherical particles of very uniform dimension. Macroscopically, the silicon dioxide pigments are recognizable as loose, white powders. Silicon dioxide pigments are sold commercially under the name Aerosil® (CAS-No. 7631-85-9) or Carb-O-Sil Advantageous Aerosil® grades are, for example, Aerosil®OX50, Aerosil®130, Aerosil®150, Aerosil®200, Aerosil®300, Aerosil®380, Aerosil®MQX 80, Aerosil® MOX 170, Aerosil®COK 84, Aerosil® R 202, Aerosil®R 805, Aerosil®R 812, Aerosil®R 972, Aerosil®R 974, Aerosil®R976.

According to the present invention, cosmetic or dermatological light protection preparations comprise 0.1 to 20% by weight, advantageously 0.5 to 10% by weight, more preferably 1 to 5% by weight, of X-ray-amorphous oxide pigments.

The non-X-ray-amorphous inorganic pigments are, according to the present invention, advantageously in hydrophobic form, i.e. have been surface-treated to repel water. This surface treatment may involve providing the pigments with a thin hydrophobic layer by processes known per se. Such a process involves, for example, producing the hydrophobic surface layer by a reaction according to

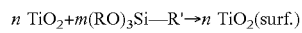

$n\ TiO_2 + m(RO)_3Si-R' \rightarrow n\ TiO_2(surf.)$ where n and m are stoichiometric parameters to be used as desired, and R and R' are the desired organic radicals. Hydrophobicized pigments prepared analogously to DE-A 33 14 742, for example, are advantageous.

For example, mention may be made of $TiO_2$ pigments, as are sold under the tradename T805 from Degussa. Preference is also given to $TiO_2/Fe_2O_3$ mixed oxides, as are supplied, for example, under the trade name T817, also from Degussa.

The total amount of inorganic pigments, in particular hydrophobic inorganic micropigments, in the finished cosmetic or dermatological preparations is advantageously chosen from the range from 0.1 to 30% by weight, preferably 0.1 to 10.0% by weight, preferably 0.5 to 6.0% by weight, based on the total weight of the preparations.

The cosmetic and/or dermatological formulations according to the present invention can have the customary composition and can be used for cosmetic and/or dermatological sun protection, and also for the treatment, care and cleansing of the skin and/or of the hair and as a make-up product in decorative cosmetics. Accordingly, the preparations according to the present invention can, depending on their formulation, be used, for example, as skin protection cream, cleansing milk, sunscreen lotion, nourishing cream, day cream or night cream, etc. In some instances, it is possible and advantageous to use the preparations according to the present invention as bases for pharmaceutical formulations. Preference is given, in particular, to those cosmetic and dermatological preparations in the form of a skin care or make-up product. Typical embodiments are creams, gels, lotions, alcoholic and aqueous/alcoholic solutions, emulsions or stick preparations. These compositions may also comprise, as further auxiliaries and additives, mild surfactants, co-emulsifiers, superfatting agents, pearlescent waxes, bodying agents, thickeners, polymers, silicone compounds, fats, waxes, stabilizers, biogenic active ingredients, deodorant active ingredients, antidandruff agents, film formers, swelling agents, hydrotropic agents, preservatives, insect repellants, tanning agents, artificial self-tanning agents (e.g. dihydroxyacetone), stabilizers, perfume oils, dyes, antimicrobial agents and the like.

For use, the cosmetic and dermatological preparations according to the present invention are applied to the skin and/or the hair in a sufficient amount in the manner customary for cosmetics.

More preference is given to those cosmetic and dermatological preparations in the form of a cosmetic composition for the protection of the skin and hair. Advantageously, in addition to UV-A, UV-B and/or broad-band filters used according to the present invention, these can contain at least one inorganic pigment, preferably an inorganic micropigment.

The cosmetic and dermatological preparations according to the present invention can comprise cosmetic auxiliaries, as are customarily used in such preparations, e.g. preservatives, bactericides, perfumes, antifoams, dyes, pigments which have a coloring action, thickeners, moisturizers and/or humectants, fats, oils, waxes or other customary constituents of a cosmetic or dermatological formulation, such as alcohols, polyols, polymers, foam stabilizers, electrolytes, organic solvents or silicone derivatives. Suitable nonionic emulsifiers or dispersants are the group formed by polyglyceryl-2 dipolyhydroxystearate (Dehymuls®PGPH), polyglyceryl-3 diisostearate (Lameform®TGI), polyglyceryl-4 isostearate (Isolan®GI 34), polyglyceryl-3 oleate, diisostearyl polyglyceryl-3 diisostearate (Isolan®PDI), polyglyceryl-3 methylglucose distearate (Tego Carey®450), polyglyceryl-3 beeswax (Cera Bellina®), polyglyceryl-4 caprate (polyglycerol caprate T2010/90), polyglyceryl-3 cetyl ether (Chimexane®NL), polyglyceryl-3 distearate (Cremophor®GS 32), polyglyceryl-2 stearate (Hostacerin®DGMS) and polyglyceryl polyricineoleate (Admul®WOL 1403), and mixtures thereof.

The amounts of cosmetic or dermatological auxiliaries and carrier substances and perfume which can be used in each case can be determined easily by the person skilled in the art by simple trial and error, depending on the nature of the product in question.

An additional content of antioxidants is generally preferred. According to the present invention, favorable antioxidants which can be used are all antioxidants customary or suitable for cosmetic and/or dermatological applications.

The antioxidants are advantageously chosen from the group of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), and also (metal) chelating agents (e.g. α-hydroxy fatty acids, palmitic acid, phytic acid, lactoferrin), (α-hydroxy acids (e.g. citric acid, lactic acid, maleic acid), humic acid, bile acid, bile extracts, bilirubin, biliverdin, EDTA, EGTA and derivatives thereof, unsaturated fatty acids and derivatives thereof (e.g. γ-linolenic acid, linoleum acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxy-toluene, butylhydroxyanisol, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of the active ingredients suitable according to the present invention.

The amount of the above-mentioned antioxidants (one or more compounds) in the preparations is preferably 0.001 to 30% by weight, more preferably 0.05 to 20% by weight, and most preferably 1 to 10% by weight, based on the total weight of the preparation.

If vitamin E and/or derivatives thereof represent the antioxidant(s), it is advantageous to choose their respective concentrations from the range from 0.001 to 10% by weight, based on the total weight of the formulation.

If vitamin A or vitamin A derivatives, or carotenes or derivatives thereof represent the antioxidant(s), it is advantageous to choose their respective concentrations from the range from 0.001 to 10% by weight, based on the total weight of the formulation.

The lipid phase can advantageously be chosen from the following group of substances:
mineral oils, mineral waxes;
oils, such as triglycerides of capric or of caprylic acid, and also natural oils, such as, for example, castor oil;
fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;

alkyl benzoate;

silicone oils, such as dimethylpolysiloxane, diethylpolysiloxane, diphenylpolysiloxane, and mixed forms thereof.

The oil phases of the emulsions, oleogels and hydrodispersions or lipodispersions for the purposes of the present invention are advantageously chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group of esters of aromatic carboxylic acids and saturated and/or unsaturated, branched and/or unbranched alcohols having a chain length of from 3 to 30 carbon atom. Such ester oils can then advantageously be chosen from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanate, 2-ethylhexyl palmitate, ethylhexyl laurate, 2-hexyl-decyl stearate, 2-octyldodecyl palmitate, oleyl oleate, oleyl erucate, erucyl oleate and synthetic, semisynthetic and natural mixtures of such esters, e.g. jojoba oil.

In addition, the oil phase can advantageously be chosen from the group of branched and unbranched hydrocarbons and hydrocarbon waxes, silicone oils, dialkyl ethers, the group of saturated or unsaturated, branched or unbranched alcohols, and fatty acid triglycerides, namely the triglycerol esters saturated and/or unsaturated, branched and/or unbranched alkanecarboxylic acids having a chain length of from 8 to 24, in particular 12 to 18, carbon atoms. The fatty acid triglycerides can, for example, advantageously be chosen from the group of synthetic, semisynthetic and natural oils, e.g. olive oil, sunflower oil, soybean oil, peanuts oil, rapeseed oil, almond oil, palm oil, coconut oil, palm kernel oil and the like.

Any mixtures of such oil and wax components are also to be used advantageously for the purposes of the present invention. It may also be advantageous in some instances to use waxes, for example cetyl palmitate, as the sole lipid component of the oil phase.

The oil phase is advantageously chosen from the group 2-ethylhexyl isostearate, octyidodecanol, isotridecyl isononanoate, isoeicosane, 2-ethylhexyl cocoate, $C_{12-15}$-alkyl benzoate, caprylic/capric triglyceride, dicapryl ether.

Particularly advantageous mixtures are those of the $C_{12-15}$-alkyl benzoate and 2-ethylhexyl isostearate, those of $C_{12-15}$-alkyl benzoate and isotridecyl isononanoate, those of the $C_{12-15}$-alkyl benzoate, 2-ethyl hexyl isostearate and isotridecyl isononanoate.

The oil phase can also advantageously have a content of cyclic or linear silicone oils or consist entirely of such oils, although it is preferable to use an additional content of their oil phase components apart from the silicone oil or silicone oils.

Cyclomethicone (octamethylcyclotetrasiloxane) is advantageously used as silicone oil to be used according to the present invention. However, other silicone oils can also be used advantageously for the purposes of the present invention, for example, hexameth-ylcyclotrisiloxane, polydimethylsiloxane, poly(methylphenylsiloxane).

Also advantageous are mixtures of cyclomethicone and isotridecyl isononanoate, and of cyclomethicone and 2-ethylhexyl isostearate.

The aqueous phase of the preparations according to the present invention optionally advantageously comprises alcohols, diols or polyols (lower alkyl), and ethers thereof, preferably ethanol, isopropanol, propylene glycol, glycerol, ethylene glycol-monoethyl or monobutyl ether, propylene glycol monomethyl, -monoethyl or monobutyl ether, diethylene glycol monomethyl or -monoethyl ether and analogous products, and also alcohols (lower alkyl), e.g. ethanol, 1,2-propanediol, glycerol, and, in particular, one or more thickeners which can advantageously be chosen from the group of silicon dioxide, aluminum silicates, polysaccharides and derivatives thereof, e.g. hyaluronic acid, xanthan gum, hydroxypropylmeth-ylcellulose, particularly advantageously from the group of polyacrylates, preferably a polyacrylate from the group of so-called Carbopols, for example, Carbopol grades 980, 981, 1382, 2984, 5984, in each case individually or in combination.

A comprehensive description of the raw materials and active ingredients used in cosmetic compositions is given in DE-A 199 19 630.

It could not have been foreseen that the indanylidene compounds according to the present invention represent an excellent selection compared with the compounds known from EP-A 823 418.

EXAMPLES

Photostability

By way of example, comparative measurements between the compounds of category A and the compounds of category B and the combination with other standard commercial UV filters such as OMC (=octyl methoxycinnamate) or BMDM (=tert-butylmethoxydibenzoyl-methane) are listed below. The substances of category B demonstrate the improvement over the substances of category A. The irradiation was carried out in a Suntester from Heraeus at an irradiation intensity of 765 W/m$^2$ (based on Global sensor). The values give the concentration decrease of the UV filters in percentage following irradiation (dose in J/cm$^2$).

Formulation according to formulation Example 1:

TABLE 1

| Compound | A1 | A2 | B1 | B2 | B3 |
|---|---|---|---|---|---|
| 72 J/cm$^2$ | 10% | 1% | 2% | 1% | 1% |
| 144 J/cm$^2$ | 13% | 6% | 3% | 2% | 2% |

Formulation according to formulation Example 12

TABLE 2

| Combination | A1 | OMC | A2 | OMC | B1 | OMC | B2 | OMC | B3 | OMC |
|---|---|---|---|---|---|---|---|---|---|---|
| 72 J/cm$^2$ | 22% | 27% | 14% | 7% | 2% | 12% | 6% | 11% | 6% | 11% |
| 144 J/cm$^2$ | 37% | 35% | 26% | 12% | 3% | 19% | 6% | 13% | 6% | 13% |

TABLE 3

| | Formulation according to: | | | | | | | |
|---|---|---|---|---|---|---|---|---|
| | Comparison without A or B | | Example 12 | | Example 4 without OMC | | Example 4 | |
| Combination | OMC | BMDM | B3 | OMC | B3 | BMDM | B3 | OMC | BMDM |
| 72 J/cm$^2$ | 48% | 68% | 6% | 11% | 2% | 5% | 3% | 17% | 35% |
| 144 J/cm$^2$ | 59% | 85% | 6% | 13% | 3% | 13% | 5% | 26% | 54% |

Compounds in Tables 1–3:

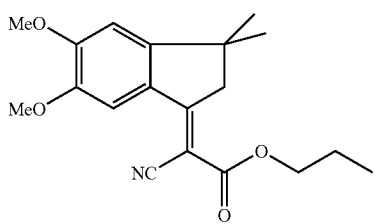
A1

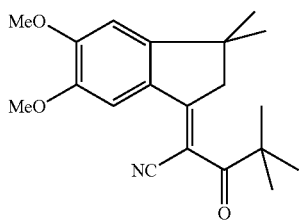
B1

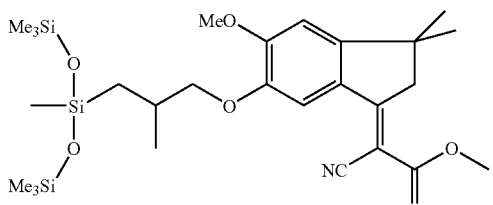
A2

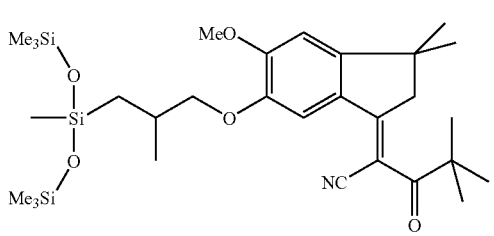
B2

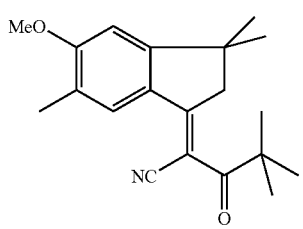
B3

Example 1

2-(5,6-Dimethoxy-3,3-dimethyl-1-indanylidene)-4,4-dimethyl-3-oxo-pentanonitrile

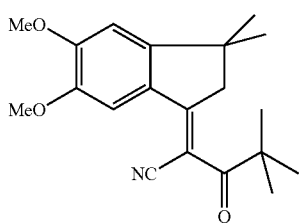

44 g (0.2 mol) of 5,6-dimethoxy-3,3-dimethyl-1-indanone, 25 g (0.2 mol) of pivaloylacetonitrile, 32 g of propionic acid and 17 g of ammonium acetate are mixed in 80 g of xylene and heated at 120° C. for 7 hours. After the system has been cooled to room temperature and the organic phase has been washed, the xylene is distilled off, and the crude product which remains is recrystallized in methanol. Yield: 50% theory; $E^{1/1}$ 730 ($\lambda_{max}$ 373 nm).

Example 2

2-(5-Methoxy-3,3,4,6-tetramethyl-1-indanylidene)-4,4-dimethyl-3-oxo-pentanonitrile

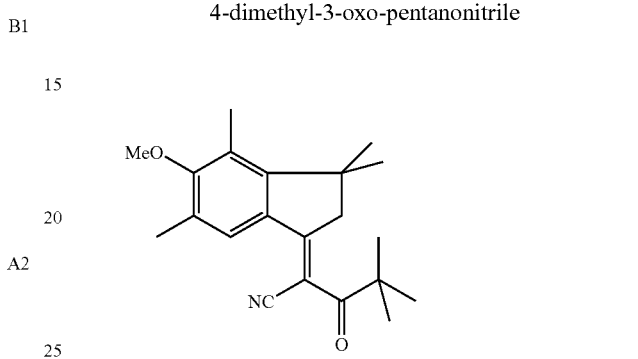

The procedure was analogous to that in Example 1 starting from 5-methoxy-3,3,4,6-tetramethyl-1-indanone. Yield: 50% of theory; $E^{1/1}$ 588 ($\lambda_{max}$ 340 nm).

Example 3

2-(3,3,5,6-tetramethyl-1-indanylidene)-4,4-dimethyl-3-oxo-pentanonitrile

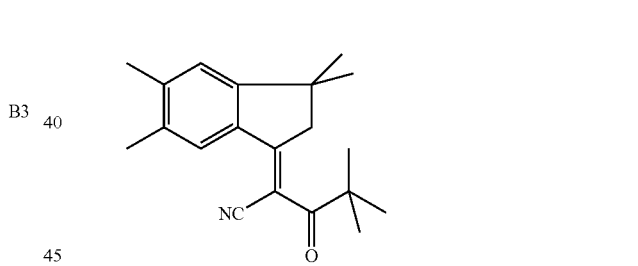

The procedure was analogous to that in Example 1 starting from 3,3,5,6-tetramethyl-1-indanone. Yield: 55% of theory; $E^{1/1}$ 630 ($\lambda_{max}$ 342 nm).

Example 4

2-(3,3,6-trimethyl-1-indanylidene)-4,4-dimethyl-3-oxo-pentanonitrile

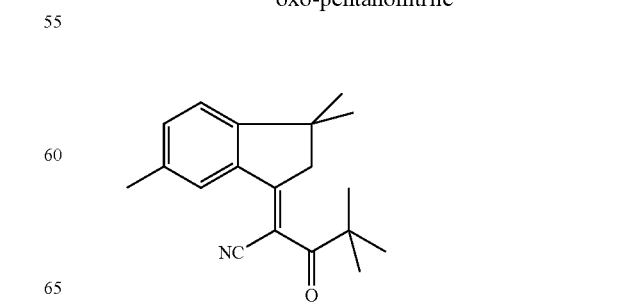

The procedure was analogous to that in Example 1 starting from 3,3,6-trimethyl-1-indanone. Yield: 45% of theory; $E^{1/1}$ 588/550 ($\lambda_{max}$ 335/316 nm).

Example 5

2-(5,6-Ethylenedioxo-3,3-dimethyl-1-indanylidene)-4,4-dimethyl-3-oxo-pentanonitrile

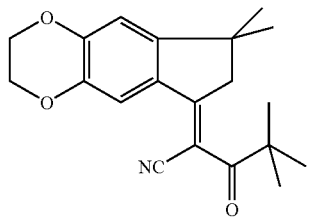

The procedure was analogous to that in Example 1 starting from 5,6-ethylenedioxo-3,3-dimethyl-1-indanone. Yield: 55% of theory; $E^{1/1}$ 640 ($\lambda_{max}$ 369 nm).

Example 6

2-(5-Methoxy-3,3,6-trimethyl-1-indanylidene)-4,4-dimethyl-3-oxo-pentanonitrile

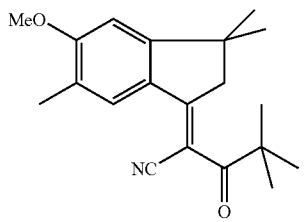

The procedure was analogous to that in Example 1 starting from 5-methoxy-3,3,6-trimethyl-1-indanone. Yield: 60% of theory; $E^{1/1}$ 850 ($\lambda_{max}$ 359 nm).

Example 7

2-[(5-Methoxy-3,3-dimethyl-(2-methyl-3-(1,3,3,3-tetramethyl-1-(trimethyl-silyloxy)-disiloxanyl)-propyl)-indanylidene)]-4,4-dimethyl-3-oxo-pentanonitrile

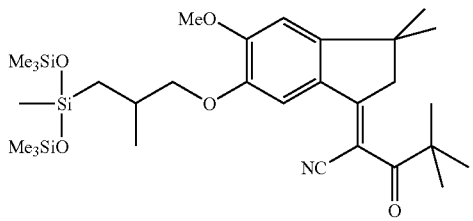

a) 2-(5-Methoxy-3,3-dimethyl-6-hydroxy-1-indanylidene)-4,4-dimethyl-3-oxo-pentanonitrile

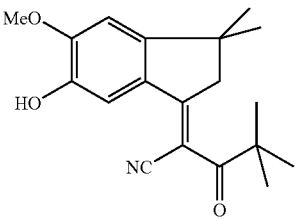

5-Methoxy-3,3-dimethyl-6-hydroxy-1-indanone is reacted according to Example 1. Yield: 50% of theory.

b) 2-(5-Methoxy-3,3-dimethyl-6-(2-methyl-propenyloxy)-1-indanylidene)-4,4-dimethyl-3-oxo-pentanonitrile

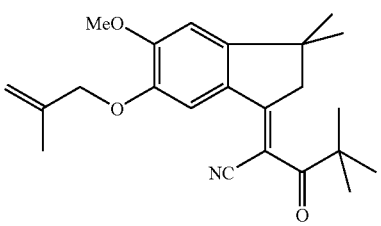

136 g (0.43 mol) of the compound under a) are added together with 95 g of potassium carbonate to 470 g of N-methylpyrrolidinone, heated to 70° C. and 42 g (0.46 mol) of methallyl chloride are added thereto over the course of 30 min. The mixture is heated for a further 3 h at 70° C., then cooled to room temperature, and the product is extracted with ethyl acetate. Yield: 45% of theory. 90 g (130 mmol) of the compound under b), 29 g (130 mmol) of 1,1,1,3,5,5,5-heptamethyltrisiloxane are kept at 80° C. in the presence of catalytic amounts of divinyltetramethylplatinum complex in 90 g of toluene and a nitrogen atmosphere for 20 h. After the solvent has been distilled off, the residue is distilled over a Kugelrohr, giving 50 g (70% of theory) of the desired product as a yellow oil; $E^{1/1}$ 400 ($\chi_{max}$ 373 nm).

Example 8

2-(6-Acetoxy-3,3-dimethyl-5-methoxy-1-indanylidene)-4,4-dimethyl-3-oxo-pentanonitrile

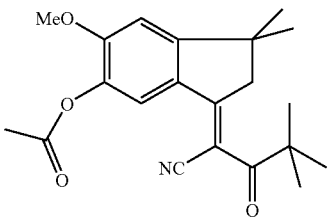

54 g (0.17 mol) of the compound under a) are reacted with 13 g (0.17 mol) of acetyl chloride in N-methylpyrrolidinone at 40° C. over the course of 5 h. Yield: 98% of theory. $E^{1/1}$ 420/280 ($\lambda_{max}$ 355/302 nm).

Example 9

2-(3,3-Dimethyl-5-tert-butyl-1-indanylidene)-3-(1'methylcyclohexyl)-3-oxo-propiononitrile

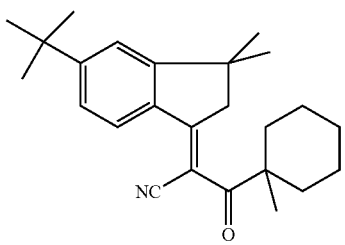

3,3-Dimethyl-5-tert-butyl-1-indanone are reacted with 3-(1'-methylcyclohexyl)-3-oxo-propiononitrile analogously to Example 1.

Yield: 40% of theory.

$E^{1/1} 380$ ($\lambda_{max} 355$ nm).

Example 10

2-(3,3,5-Trimethyl-1-indanylidene)-3-phenyl-3-oxo-propiononitrile

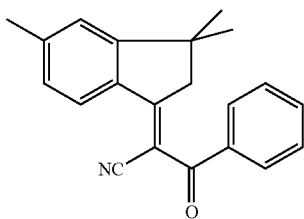

3,3,5-Trimethyl-1-indanone are reacted with benzoylacetonitrile analogously to Example 1.

Yield: 50% of theory.

$E^{1/1} 600$ ($\lambda_{max} 350$ nm).

Formulation Example 1

Sunscreen Soft Cream (O/W), In-vitro SPF 3, Water Resistant

TABLE 4

| Part | Raw Materials | INCI Name | % (wt.) |
|---|---|---|---|
| A | Crodafos MCA | Cetyl Phosphate | 1.50 |
|   | Cutina MD | Glyceryl Stearate | 2.00 |
|   | Copherol 1250 | Tocopheryl Acetate | 0.50 |
|   | Lanette 16 | Cetyl Alcohol | 1.00 |
|   | Tegosoft TN | C12–15 Alkyl Benzoate | 24.00 |
|   | Prisorine 3505 | Isostearic Acid | 1.00 |
|   | UV absorber according to formula I |  | 3.00 |
| B | Water, dist. | Water (Aqua) | 59.60 |
|   | EDETA B liq. | Tetrasodium EDTA | 0.20 |
|   | Glycerol, 99% | Glycerin | 3.00 |
|   | Phenoxyethanol | Phenoxyethanol | 0.70 |
|   | Solbrol M | Methylparaben | 0.20 |
|   | Solbrol P | Propylparaben | 0.10 |
|   | Carbopol ETD 2050 | Carbomer | 0.20 |
| C | Sodium hydroxide solution, 10% aq. | Sodium Hydroxide | 2.70 |
| D | Perfume oil | Parfum (Fragrance) | 0.30 |

Preparation method

Part A: Heat to about 85° C.

Part B: Weigh in raw materials without Carbopol. Disperse Carbopol therein using Ultra Turrax. Heat to about 85° C. Add B to A.

Part C: Immediately add to A/B and then homogenize while hot (Ultra Turrax). Leave to cool with stirring.

Part D: Add and stir in.

TABLE 5

| | |
|---|---|
| in-vitro SPF (Labsphere Ultraviolet Transmittance Analyzer) | 3 |
| Boots star rating | 4 |
| Broad spectrum rating (Diffey) | 4 |
| Critical wavelength (90% absorption at λ in nm) | 385 |
| UV filter substantivity after watering | 97% |

Formulation Example 2

Sunscreen Lotion (O/W), In-vitro SPF 20

TABLE 6

| Part | Raw Materials | INCI Name | % (wt.) |
|---|---|---|---|
| A | Crodafos MCA | Cetyl Phosphate | 1.50 |
|   | Cutina MD | Glyceryl Stearate | 2.00 |
|   | Copherol 1250 | Tocopheryl Acetate | 0.50 |
|   | Lanette 16 | Cetyl Alcohol | 1.00 |
|   | Tegosoft TN | C12–15 Alkyl Benzoate | 10.60 |
|   | Prisorine 3505 | Isostearic Acid | 1.00 |
|   | UV absorber according to formula I |  | 2.00 |
|   | Neo Heliopan ® AV | Ethylhexyl Methoxycinnamate | 5.00 |
| B | Water, dist. | Water (Aqua) | 55.07 |
|   | EDETA B fl. | Tetrasodium EDTA | 0.20 |
|   | Glycerol, 99% | Glycerin | 3.00 |
|   | Phenoxyethanol | Phenoxyethanol | 0.70 |
|   | Solbrol M | Methylparaben | 0.20 |
|   | Solbrol P | Propylparaben | 0.10 |
|   | Carbopol ETD 2050 | Carbomer | 0.20 |
| C | Sodium hydroxide solution, 10% aq. | Sodium hydroxide | 3.30 |
|   | Neo Heliopan ® Hydro, 15% strength solution neutralized with NaOH | Phenylbenzimidazole Sulfonic Acid | 13.33 |
| D | Perfume oil | Parfum (Fragrance) | 0.30 |

Preparation method

Part A: Heat to about 85° C.

Part B: Weigh in raw materials without Carbopol. Disperse Carbopol therein using Ultra Turrax. Heat to about 85° C. Add B to A.

Part C: Immediately add to A/B and then homogenize while hot (Ultra Turrax). Leave to cool with stirring.

Part D: Add and stir in.

TABLE 7

| | |
|---|---|
| in-vitro SPF (Labsphere Ultraviolet Transmittance Analyzer) | 20 |
| Boots star rating | 2 |
| Broad spectrum rating (Diffey) | 4 |
| Critical wavelength (90% absorption at λ in nm) | 378 |

Formulation Example 3

Sunscreen Milk (O/W), In-vitro SPF 6

TABLE 8

| Part | Raw Materials | INCI Name | % (wt.) |
|---|---|---|---|
| A | Tegin M | Glyceryl Stearate | 2.50 |
|   | Tagat S | PEG-30 Glyceryl Stearate | 1.95 |
|   | Lanette O | Cetearyl Alcohol | 2.20 |
|   | Copherol 1250 | Tocopheryl Acetate | 0.50 |
|   | Miglyol 8810 | Butylene Glycol Dicaprylate/Caprate | 12.00 |
|   | Tegosoft TN | C12–C15 Alkyl Benzoate | 8.00 |
|   | Phenonip | Phenoxyethanol (and) methylparaben (and) Butylparaben (and) ethylparaben (and) Propylparaben | 0.15 |
|   | UV absorber according to formula I |  | 5.00 |
| B | Water, dist. | Water (Aqua) | 43.90 |
|   | EDETA BD | Disodium EDETA | 0.10 |
|   | 1,2-Propylene glycol | Propylene Glycol | 2.00 |
|   | Phenonip | Phenoxyethanol (and) Methylparaben (and) Butylparaben (and) Ethylparaben (and) Propylparaben | 0.30 |
| C | Water, dist. | Water (Aqua) | 19.00 |
|   | Carbopol 2050 | Carbomer | 0.40 |
|   | NaOH, 10% strength | Sodium Hydroxide | 1.70 |
| D | Perfume oil | Parfum (Fragrance) | 0.30 |

Preparation method
Part A: Heat to 80–85° C.
Part B: Heat to 80–85° C., add part B to part A with stirring.
Part C: Disperse Carbopol into the water and neutralize with NaOH, with stirring. Add part C at about 60° C. with stirring. Allow to cool to RT.
Part D: Add and stir.

TABLE 9

| | |
|---|---|
| in-vitro SPF (Labsphere Ultraviolet Transmittance Analyzer) | 6 |
| Boots Star Rating | 4 |
| Broad Spectrum Rating (Diffey) | 4 |
| Critical wavelength (90% absorption at λ in nm) | 385 |

Formulation Example 4

Sunscreen Lotion (O/W), In-vitro SPF 21

TABLE 10

| Part | Raw Materials | INCI Name | % (wt.) |
|---|---|---|---|
| A | Tegin M | Glyceryl Stearate | 2.50 |
|   | Tagat S | PEG-30 Glyceryl Stearate | 1.95 |
|   | Lanette O | Cetearyl Alcohol | 2.20 |
|   | Copherol 1250 | Tocopheryl Acetate | 0.50 |
|   | Miglyol 8810 | Butylene Glycol Dicaprylate/Caprate | 12.00 |
|   | Tegosoft TN | C12–C15 Alkyl Benzoate | 8.00 |
|   | Phenonip | Phenoxyethanol (and) Methylparaben (and) Butylparaben (and) Ethylparaben (and) Propylparaben | 0.20 |
|   | UV absorber according to formula I |  | 2.00 |
|   | Neo Heliopan ® AV | Ethylhexyl methoxycinnamate | 5.00 |
|   | Neo Heliopan ® 357 | Butyl methoxy-dibenzoylmethane | 1.00 |
| B | Water, dist. | Water (Aqua) | 39.35 |
|   | EDETA BD | Disodium EDETA | 0.10 |
|   | 1,2-Propyleneglycol | Propylene Glycol | 2.00 |
|   | Phenonip | Phenoxyethanol (and) Methylparaben (and) Butylparaben (and) Ethylparaben (and) Propylparaben | 0.30 |
|   | Vitamin C | Ascorbic Acid | 0.10 |
| C | Water, dist. | Water (Aqua) | 20.00 |
|   | Carbopol 2050 | Carbomer | 0.40 |
|   | NaOH, 10% strength | Sodium Hydroxide | 1.70 |
| D | Perfume oil | Parfum (Fragrance) | 0.30 |

Preparation method
Part A: Heat to 80–85° C.
Part B: Heat to 80–85° C., add part B to part A with stirring.
Part C: Disperse Carbopol into the water and neutralize with NaOH, with stirring. Add part C at about 60° C. with stirring. Allow to cool to RT.
Part D: Add and stir.

TABLE 11

| | |
|---|---|
| in-vitro SPF (Labsphere Ultraviolet Transmittance Analyzer) | 21 |
| Boots Star Rating | 3 |
| Broad Spectrum Rating (Diffey) | 4 |
| Critical wavelength (90% absorption at λ in nm) | 379 |

Formulation Example 5

Sunscreen Lotion (O/W), In-vitro SPF 11

TABLE 12

| Part | Raw Materials | INCI Name | % (wt.) |
|---|---|---|---|
| A | Eumulgin VL 75 | Lauryl Glucoside (and) Polyglyceryl-2-Dipolyhydroxystearate (and) Glycerin | 3.00 |
|   | Tegosoft TN | C12–25 Alkyl Benzoate | 20.00 |
|   | Copherol 1250 | Tocopheryl Acetate | 0.50 |
|   | UV absorber according to formula I |  | 3.00 |
|   | Perfume oil | Parfum (Fragrance) | 0.20 |
|   | Neo Heliopan ® 303 | Octocrylene | 5.00 |
|   | Carbopol 2984 | Carbomer | 0.35 |
|   | Pemulen TR-1 | Acrylates/C10–30 Alkyl Acrylate Crosspolymer | 0.15 |
| B | Water, dist. | Water (Aqua) | 60.50 |
|   | EDETA BD | Disodium EDTA | 0.10 |
|   | Glycerol, 99% | Glycerin | 5.00 |
|   | Phenoxyethanol | Phenoxyethanol | 0.70 |
|   | Solbrol M | Methylparaben | 0.20 |
|   | Solbrol P | Propylparaben | 0.10 |
| C | NaOH, 10% strength | Sodium Hydroxide | 1.20 |

Preparation method
Part A: Dissolve UV absorber according to formula I in the oils or liquid UV filters (heating to about 70° C.). Allow to cool to about 30° C., add the remaining constituents apart from Carbopol and Pemulen and mix at room temperature (stir for about 5 minutes). Stir in Carbopol and Pemulen.
Part B: Dissolve Solbrols in phenoxyethanol with heating. Mix with water and glycerol, add to part A with stirring. Stir for about 60 minutes.
Part C: Add to A/B, homogenize using the Ultra Turrax.

TABLE 13

| | |
|---|---|
| in-vitro SPF (Labsphere Ultraviolet Transmittance Analyzer) | 11 |
| Boots Star Rating | 4 |
| Broad Spectrum Rating (Diffey) | 4 |
| Critical wavelength (90% Absorption at λ in nm) | 382 |

Formulation Example 6

Sunscreen Cream (W/O), In-vitro SPF 4, Water Resistant

TABLE 14

| Part | Raw Materials | INCI Name | % (wt.) |
|---|---|---|---|
| A | Dehymuls PGPH | Polyglyceryl-2 Dipolyhydroxystearate | 5.00 |
| | Copherol 1250 | Tocopheryl Acetate | 0.50 |
| | Permulgin 3220 | Ozokerite | 0.50 |
| | Zinc stearate | Zinc Stearate | 0.50 |
| | Tegosoft TN | C12–15 Alkyl Benzoate | 25.00 |
| | UV absorber according to formula I | | 5.00 |
| B | Water, dist. | Water (Aqua) | 57.90 |
| | EDETA BD | Disodium EDTA | 0.10 |
| | Glycerol, 99% | Glycerin | 4.00 |
| | Phenoxyethanol | Phenoxyethanol | 0.70 |
| | Solbrol M | Methylparaben | 0.20 |
| | Solbrol P | Propylparaben | 0.10 |
| | Magnesium sulfate | Magnesium Sulfate | 0.50 |

Preparation method
Part A: Heat to about 85° C.
Part B: Heat to about 85° C. (without zinc oxide; disperse zinc oxide therein using the Ultra Turrax).
Add B to A.
Allow to cool with stirring, then homogenize.

TABLE 15

| | |
|---|---|
| in-vitro SPF (Labsphere Ultraviolet Transmittance Analyzer) | 4 |
| Boots Star Rating | 4 |
| Broad Spectrum Rating (Diffey) | 4 |
| Critical wavelength (90% Absorption at λ in nm) | 384 |
| UV filter substantivity after watering | 95% |

Formulation Example 7

Sunscreen Softcream (W/O), In-vitro SPF 40

TABLE 16

| Part | Raw Materials | INCI Name | % (wt.) |
|---|---|---|---|
| A | Dehymuls PGPH | Polyglyceryl-2 Dipolyhydroxystearate | 5.00 |
| | Copherol 1250 | Tocopheryl Acetate | 0.50 |
| | Permulgin 3220 | Ozokerite | 0.50 |
| | Zinc stearate | Zinc Stearate | 0.50 |
| | Tegosoft TN | C12–15 Alkyl Benzoate | 10.00 |
| | UV absorber according to formula I | | 2.00 |
| | Neo Heliopan ® 303 | Octocrylene | 5.00 |
| | Neo Heliopan ® MBC | 4-Methylbenzylidene Camphor | 3.00 |
| | Zinc oxide neutral H&R | Zinc Oxide | 5.00 |
| B | Water, dist. | Water (Aqua) | 62.90 |
| | EDETA BD | Disodium EDTA | 0.10 |
| | Glycerol, 99% | Glycerin | 4.00 |
| | Phenoxyethanol | Phenoxyethanol | 0.70 |
| | Solbrol M | Methylparaben | 0.20 |
| | Solbrol P | Propylparaben | 0.10 |
| | Magnesium sulfate | Magnesium Sulfate | 0.50 |
| C | Parfume oil | Parfum (Fragrance) | 0.20 |

Preparation method
Part A: Heat to about 85° C.
Part B: Heat to about 85° C. (without zinc oxide; disperse zinc oxide therein using the Ultra Turrax).
Add B to A.
Allow to cool with stirring.
Part C: Add and then homogenize

TABLE 17

| | |
|---|---|
| in-vitro SPF (Labsphere Ultraviolet Transmittance Analyzer) | 40 |
| Boots Star Rating | 3 |
| Broad Spectrum Rating (Diffey) | 4 |
| Critical wavelength (90% Absorption at λ in nm) | 379 |

Formulation Example 8

Sunscreen milk (W/O)

TABLE 18

| Part | Raw Materials | INCI Name | % (wt.) |
|---|---|---|---|
| A | Dehymuls PGPH | Polyglyceryl-2 Dipolyhydroxystearate | 3.00 |
| | Beeswax 8100 | Beeswax | 1.00 |
| | Monomuls 90-0-18 | Glyceryl Oleate | 1.00 |
| | Zinc stearate | Zinc stearate | 1.00 |
| | Cetiol SN | Cetearyl Isononanoate | 5.00 |
| | Cetiol OE | Dicaprylyl Ether | 5.00 |
| | Tegosoft TN | C12–15 Alkyl Benzoate | 4.00 |
| | Copherol 1250 | Tocopheryl Acetate | 0.50 |
| | Solbrol P | Propylparaben | 0.10 |
| | Neo Heliopan ® OS | Ethylhexyl Salicylate | 5.00 |
| | Neo Heliopan ® AV | Ethylhexyl Methoxycinnamate | 7.50 |
| | UV absorber according to formula I | | 1.50 |
| B | Water, dist. | Water (Aqua) | 44.10 |
| | Trilon BD | Disodium EDTA | 0.10 |
| | Glycerol, 99% | Glycerin | 5.00 |
| | Solbrol M | Methylparaben | 0.20 |
| | Phenoxyethanol | Phenoxyethanol | 0.70 |
| | Neo Heliopan ® AP 10% strength solution neutralized with NaOH | Disodium Phenyl Dibenzimidazole Tetrasulfonate | 15.00 |
| C | Perfume oil | Parfum (Fragrance) | 0.30 |
| | Bisabolol | Bisabolol | 0.10 |

Preparation method
Part A: Heat to about 85° C.
Part B: Heat to about 85° C. Add B to A. Allow to cool with stirring.
Part C: Add and then homogenize.

Formulation Example 9

Daycare Cream with UV protection

TABLE 19

| Part | Raw Materials | INCI Name | % (wt.) |
|---|---|---|---|
| A | Emulgade PL 68/50 | Cetearyl Glycoside (and) Cetearyl Alcohol | 4.50 |
|  | Cetiol PGL | Hexyldecanol (and) Hexyldecyl Laurate | 8.00 |
|  | Myritol 331 | Cocoglycerides | 8.00 |
|  | Copherol 1250 | Tocopheryl Acetate | 0.50 |
|  | Neo Heliopan ® E1000 | Isoamylp- Methoxycinnamate | 2.00 |
|  | UV absorber according to formula I |  | 2.00 |
| B | Water, dist. | Water (Aqua) | 45.40 |
|  | Glycerol | Glycerin | 3.00 |
|  | Phenonip | Phenoxyethanol (and) Methylparaben (and) Butyparaben (and) Ethyparaben (and) Propylparaben | 0.50 |
| C | Water, dist. | Water (Aqua) | 25.00 |
|  | Carbopol ETD 2050 | Carbomer | 0.20 |
|  | NaOH, 10% strength | Sodium Hydroxide | 0.60 |
| D | Perfume oil | Parfum (Fragrance) | 0.30 |

Preparation method
Part A: Heat to 80° C.
Part B: Heat to 80° C. Add to part A with stirring.
Part C: Disperse Carbopol in water and neutralize with sodium hydroxide solution. Add to part A/B at about 55° C.
Part D: Add at RT and homogenize.

Formulation Example 10

Sunscreen Spray

TABLE 20

| Part | Raw Materials | INCI Name | % (wt.) |
|---|---|---|---|
| A | Water, demin. | Water (Aqua) | 69.50 |
|  | Glycerol, 99% | Glycerin | 4.00 |
|  | 1,3 Butylene glycol | Butylene Glycol | 5.00 |
|  | D-Panthenol | Panthenol | 0.50 |
|  | Lara Care A-200 | Galactoarabinan | 0.25 |
| B | Baysilone oil M 10 | Dimethicone | 1.00 |
|  | Edeta BD | Disodium EDTA | 0.10 |
|  | Copherol 1250 | Tocopheryl Acetate | 0.50 |
|  | Cetiol OE | Dicaprylyl Ether | 3.00 |
|  | Neo Heliopan ® HMS | Homosalate | 5.00 |
|  | Neo Heliopan ® AV | Ethylhexyl Methoxycinnamate | 6.00 |
|  | Neo Heliopan ® 357 | Butyl Methoxydibenzoylmethane | 1.00 |
|  | UV absorber according to formula I |  | 2.00 |
|  | alpha-bisabolol nat. H&R | Bisabolol | 0.10 |
|  | Pemulen TR-2 | Acrylates/C10–30 Alkyl Acrylate Crosspolymer | 0.25 |
| C | Phenoxyethanol | Phenoxyethanol | 0.70 |
|  | Solbrol M | Methylparaben | 0.20 |
|  | Solbrol P | Propylparaben | 0.10 |
| D | NaOH, 10% strength | Sodium Hydroxide | 0.60 |
| E | Perfume oil | Fragrance (Parfum) | 0.20 |

Preparation method
Part A: Dissolve Lara Care A-200 into the other constituents of part A with stirring.
Part B: Weigh in all raw materials (without Pemulen) and dissolve the crystalline substances with heating. Disperse Pemulen therein.
Add part B to part A then homogenize for 1 minute.
Add part C + D and homogenize again for 1–2 minutes using the Ultra Turrax.

Formulation Example 11

Sunscreen Hydrodispersion Gel (Balm)

TABLE 21

| Part | Raw Materials | INCI Name | % (wt.) |
|---|---|---|---|
| A | Water, dist. | Water (Aqua) | 74.90 |
|  | Carbopol 1342 | Acrylates/C10–30 Alkyl Acrylate Crosspolymer | 1.00 |
|  | Triethanolamine | Triethanolamine | 1.20 |
| B | Neo Heliopan ® Hydro, 30% strength solution neutralized with TEA | Phenylbenzimidazole Sulfonic Acid | 10.00 |
| C | Neo Heliopan ® AV | Ethylhexyl Methoxycinnamate | 3.00 |
|  | UV absorber according to formula I |  | 2.00 |
|  | Isopropyl myristate | Isopropyl Myristate | 4.00 |
|  | Baysilone oil PK 20 | Phenyl Trimethicone | 3.00 |
|  | Phenonip | Phenoxyethanol (and) Methylparaben (and) Butyparaben (and) Ethyparaben (and) Propylparaben | 0.50 |
|  | Perfume oil | Parfum (Fragrance) | 0.30 |
|  | Bisabolol nat. H&R | Bisabolol | 0.10 |

Preparation method
Part A: Disperse Carbopol in water and neutralize with sodium hydroxide solution.
Part B: Add to part A with stirring.
Part C: Dissolve crystalline constituents in the other raw materials of part C with warming (max. 40° C.) and add to part A/B. Stir well and then homogenize. (Homozenta).

Formulation Example 12

Hair Conditioner with UV Filters

TABLE 22

| Part | Raw Materials | INCI Name | % (wt.) |
|---|---|---|---|
| A | Emulgade 1000 NI | Cetearyl Alcohol (and) Ceteareth-20 | 2.00 |
|  | Lanette 16 | Cetyl Alcohol | 1.00 |
|  | Neo Heliopan ® AV | 2-Ethylhexyl Methoxycinnamate | 3.00 |
|  | UV absorber according to formula I |  | 1.00 |
| B | Water, dist. | Water (Aqua) | 91.70 |
|  | Edeta BD | Disodium EDTA | 0.10 |
|  | Phenonip | Phenoxyethanol (and) Methylparaben (and) Butyparaben (and) Ethyparaben (and) Propylparaben | 0.40 |
|  | Dehyquart A-CA | Cetrimonium Chloride | 0.20 |
|  | NaOH, 1% strength | Sodium Hydroxide | 0.30 |
| C | Perfume oil | Parfum (Fragrance) | 0.30 |

Preparation method
Part A: Heat to 80° C.
Part B: Heat to 80° C. Add to part A with stirring.
Part C: Add at 40° C. and cool to RT.

Formulation Example 13

Sunscreen Lotion (O/W)

TABLE 23

| Part | Raw Materials | INCI Name | % (wt.) |
|---|---|---|---|
| A | Tegin M | Glyceryl Stearate | 2.50 |
|   | Tagat S | PEG-30 Glyceryl Stearate | 1.95 |
|   | Lanette O | Cetearyl Alcohol | 2.20 |
|   | Hallbrite TQ | Diethylhexyl Naphthalate | 7.00 |
|   | Cetiol B | Dibutyl Adipate | 5.00 |
|   | Tegosoft TN | C12–C15 Alkylbenzoate | 4.00 |
|   | Myritol PC | Propylene Glycol Dicaprylate/Dicaprate | 4.00 |
|   | Phenonip | Phenoxyethanol (and) Methylparaben (and) Butylparaben (and) Ethylparaben (and) Propylparaben | 0.15 |
|   | UV absorber according to formula I |   | 2.00 |
|   | Neo Heliopan ® AV | Ethylhexyl Methoxycinnamate | 5.00 |
| B | Water, dist. | Water (Aqua) | 42.80 |
|   | 1,2-Propylene glycol | Propylene Glycol | 2.00 |
|   | Phenonip | Phenoxyethanol (and) Methylparaben (and) Butylparaben (and) Ethylparaben (and) Propylparaben | 0.30 |
| C | Water, dist. | Water (Aqua) | 19.00 |
|   | Carbopol 2050 | Carbomer | 0.40 |
|   | NaOH, 10% strength | Sodium Hydroxide | 1.70 |

Preparation method
Part A: Heat to 80–85° C.
Part B: Heat to 80–85° C., add part B to part A with stirring.
Part C: Disperse Carbopol into the water and neutralize with NaOH with stirring. Add part C at about 60° C. with stirring.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An indanylidene compound according to the formula

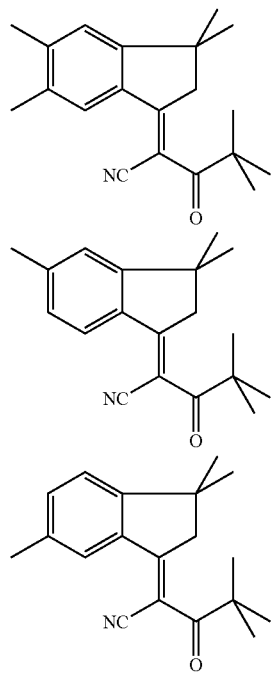

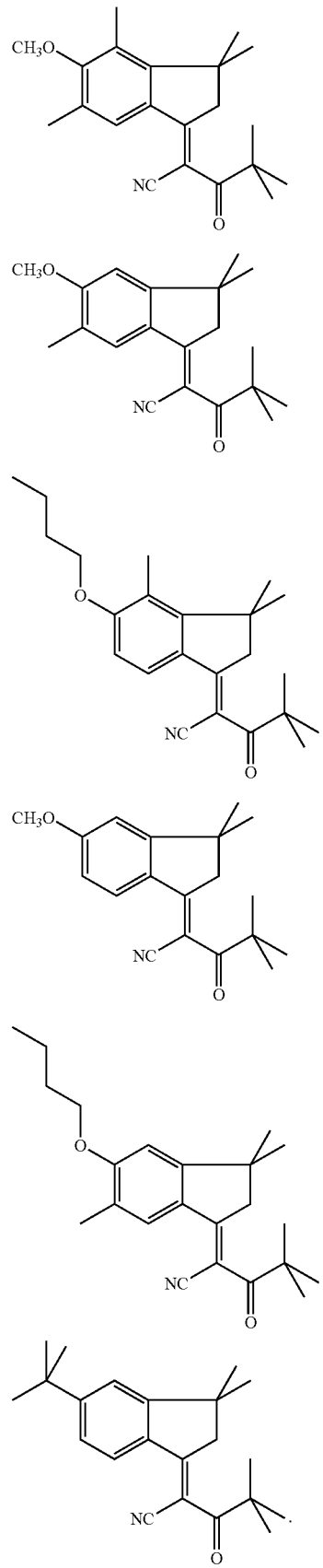

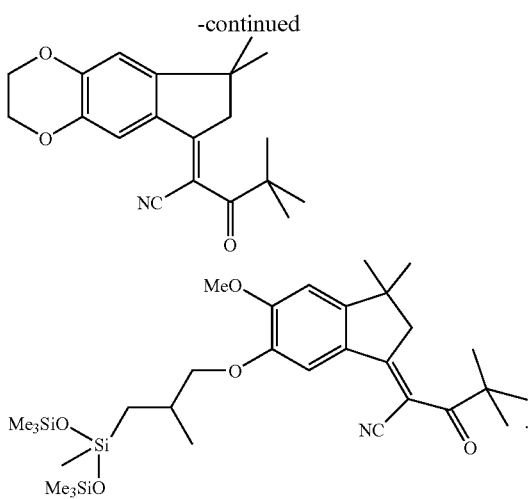

2. A UV absorber mixture comprising one or more indanylidene compounds according to claim 1.

3. A mixture comprising a UV absorber which comprises one or more indanylidene compounds according to claim 1.

4. An indanylidene compound selected from the group consisting of 2-(5-methoxy-3,3,4,6-tetramethyl-1-indanylidene)-4,4-dimethyl-3-oxo-pentanonitrile, 2-(3,3,6-tetramethyl-1-indanylidene)-4,4-dimethyl-3-oxo-pentanonitrile, 2-(3,3,5,6-trimethyl-1-indanylidene)-4,4-dimethyl-3-oxo-pentanonitrile, 2-(5,6-ethoxylenedioxo-3,3-dimethyl-1-indanylidene)-4,4-dimethyl-3-oxo-pentanonitrile, 2-(5-methoxy-3,3,6-trimethyl-1-indanylidene)-4,4-dimethyl-3-oxo-pentanonitrile, 2-(5-methyl-3,3-dimethyl-1-indanylidene)-4,4-dimethyl-3-oxo-pentanonitrile, 2-(5-methoxy-3,3-dimethyl-1-indanylidene)-4,4dimethyl-3-oxo-pentanonitrile, 2-(5-t-butyl-3,3-dimethyl-1indanylidene)-4,4-dimethyl-3-oxo-pentanonitrile, 2-(5-n-butoxy-3,3,4-trimethyl-1-indanylidene)-4,4-dimethyl-3-oxo-pentanonitrile, 2-(5-n-butoxy-3,3,6-trimethyl-1-indanylidene)-4,4-dimethyl-3-oxo-pentanonitrile, 2-[(5-methoxy-3,3-dimethyl-(2-methyl-3-(1,3,3,3-tetramethyl-1-(trimethyl -silyloxy)-disiloxanyl)-propyl)-indanylidene)]-4,4-dimethyl-3-oxo-pentanonitrile, and 2-(6-acetoxy-3,3-dimethyl-5-methoxy-1-indanylidene)-4,4-dimethyl-3-oxo-pentanonitrile.

5. A UV absorber mixture comprising a compound of the formula

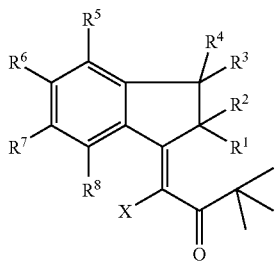

in which $R^1$ to $R^4$ independently of one another are hydrogen, $C_1$–$C_{20}$-alkyl or $C_5$–$C_{10}$cycloalkyl, with the proviso that two substituents on adjacent carbon atoms can together also be an optionally substituted $C_1$–$C_4$-alkylene group forming a ring;

may also, independently of one another, be $C_2$–$C_{20}$-alkyl, in which at least one methylene group may be replaced by oxygen, $C_3$–$C_{20}$-alkenyl, $C_3$–$C_{20}$-alkynyl or a group S, where S may be a silane, an oligosiloxane or a polysiloxane group;

$R^5$ to $R^8$, independently of one another, are hydrogen, $C_1$–$C_{20}$-alkyl or $C_5$–$C_{10}$-cycloalkyl or $C_1$–$C_{20}$-alkoxy, $C_5$–$C_{10}$-cycloalkoxy, hydroxyl, acetoxy, acetamino, carboxyl, carbalkoxy or carbamoyl, additionally two substituents of $R^5$ to $R^8$ on adjacent carbon atoms can together form a 5–7-membered ring which contains up to three heteroatoms, where the ring atoms may be substituted by exocyclically doubled-bonded oxygen (keto group), also, in the case of alkoxy, may, independently of one another, be $C_2$–$C_{20}$-alkyl in which at least one methylene group may be replaced by oxygen, $C_3$–$C_{20}$-alkenyl, $C_3$–$C_{20}$-alkynyl or a group S, where S may be a silane, an oligosiloxane or a polysiloxane group;

X is cyano, $CON(R)_2$ or $CO_2R$, where R is hydrogen or $C_1$–$C_8$-alkyl;

and one or more UV absorbers having a methoxycinnamate structure, a dibenzoylmethane structure, or derivatives thereof.

6. A cosmetic composition for protecting skin and hair, comprising indanylidene compounds of the formula

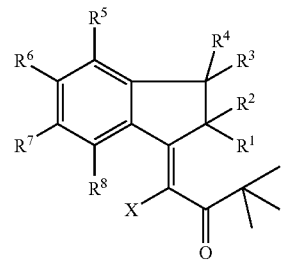

in which $R^1$ to $R^4$, independently of one another are hydrogen, $C_1$–$C_{20}$-alkyl or $C_5$–$C_{10}$-cycloalkyl, with the proviso that two substituents on adjacent carbon atoms can together also be an optionally substituted $C_1$–$C_4$-alkylene group forming a ring;

may also, independently of one another, be $C_2$–$C_{20}$-alkyl, in which at least one methylene group may be replaced by oxygen, $C_3$–$C_{20}$-alkenyl, $C_3$–$C_{20}$-alkynyl or a group S, where S may be a silane, an oligosiloxane or a polysiloxane group;

$R^5$ to $R^8$, independently of one another, are hydrogen, $C_1$–$C_{20}$-alkyl or $C_5$–$C_{10}$cycloalkyl or $C_1$–$C_{20}$-alkoxy, $C_5$–$C_{10}$-cycloalkoxy, hydroxyl, acetoxy, acetamino, carboxyl, carbalkoxy or carbamoyl, additionally two substituents of $R^5$ to $R^8$ on adjacent carbon atoms can together form a 5–7-membered ring which contains up to three heteroatoms, in particular oxygen or nitrogen, where the ring atoms may be substituted by exocyclically doubled-bonded oxygen (keto group), also, in the case of alkoxy, may, independently of one another, be $C_2$–$C_{20}$-alkyl in which at least one methylene group may be replaced by oxygen, $C_3$–$C_{20}$-alkenyl, $C_3$–$C_{20}$-alkynyl or a group S, where S may be a silane, an oligosiloxane or a polysiloxane group;

X is cyano, $CON(R)_2$ or $CO_2R$, where R is hydrogen or $C_1$–$C_8$-alkyl.

7. The cosmetic composition for protecting skin and hair according to claim 6, comprising 2-(5,6-dimethoxy-3,3-dimethyl-1-indanylidene)-4,4-dimethyl -3-oxo-pentanonitrile, 2-(5-methoxy-3,3,4,6-tetramethyl -1-indanylidene)-4,4-dimethyl -3-oxo-pentanonitrile, 2-(3,3,5,6-tetramethyl-1-indanylidene)-4,4-dimethyl-3-oxo -pentanonitrile, 2-(3,3,6-trimethyl-1-indanylidene)-4,4-dimethyl-3-oxo-pentanonitrile, 2-(5,6-ethylenedioxo-3,3dimethyl-1-indanylidene)-4,4-dimethyl-3-oxo-pentanonitrile, 2-(5-methoxy-3,3,6-trimethyl-1-indanylidene)-4,4-dimethyl-3-oxo-pentanonitrile, 2[(5-methoxy-3,3-dimethyl-(2-methyl-3-(1,3,3,3-tetramethyl-1-(trimethyl-silyloxy) -disiloxanyl)-propyl)-indanylidene)]-4,4-dimethyl-3-oxo-pentanonitrile, or 2-(6-acetoxy-3,3-dimethyl-5-methoxy-1-indanylidene)-4,4-dimethyl-3-oxo-pentanonitrile.

8. The cosmetic composition according to claim 6, wherein said indanylidene compound is a UV absorber and protects the skin and/or the hair against UV radiation.

9. The cosmetic composition according to claim 6, wherein said composition further comprises at least one tanning agent and/or artificial self-tanning agent for the skin.

10. The cosmetic composition according to claim 6, wherein said composition further comprises one or more further UV absorbers.

11. The cosmetic composition according to claim 6, wherein said composition further comprises one or more other UV absorbers selected from the group consisting of ethylhexylmethoxy cinnamate, 2-ethylhexyl-2-cyano-3,3-diphenyl acrylate, 2-phenylbenzimidazolesulphonic acid, methylbenzylidene camphor, 4-t-butyl-4'-methoxy-dibenzoylmethane, phenylene-bis-benzimidazyl-tetrasulphonic acid disodium salt, terephthalylidene-dibornanesulphonic acid and salts thereof, phenol, 2-(2H -benzotriazol-2-yl)-4-methyl-6-(2-methyl-3(1,3,3,3-tetramethyl-1-(trimethylsilyl)-oxy) -disiloxyanyl)-propyl), benzylidene malonate polysiloxane, 2,2'-methylene-bis-(6-(2H -benzotriazol-2-yl)-4-1,1,3,3-tetramethylbutyl)-phenol), 2,4-bis[{(4-(2-ethylhexyloxy-2-hydroxy}-phenyl]-6-(4-methoxyphenyl)-1,3,5-triazine, 4,4',4-(1,3,5-triazine-2,4,6-triyltriimino)-tris-benzoic acid tris(2-ethylhexyl ester), 4,4'-[(6-[4-(1,1-dimethyl) -aminocarbonyl)-phenylamino]-1,3,5-triazine-2,4-diyl)diimino]-bis-(benzoic acid-2-ethylhexyl ester), zinc oxide and titanium dioxide.

12. The cosmetic composition according to claim 6, wherein said composition further comprises UV absorbers and additionally coated or noncoated pigments or nanopigments of metal oxides.

13. The cosmetic composition according to claim 6, wherein said composition further comprises UV absorbers and additionally finely divided pigments such that a UV broad-band protection performance with a critical wavelength $\lambda_{crit}$>380 nm results therefrom.

14. A cosmetic composition for protecting skin and hair, comprising one or more indanylidene compounds of the formula:

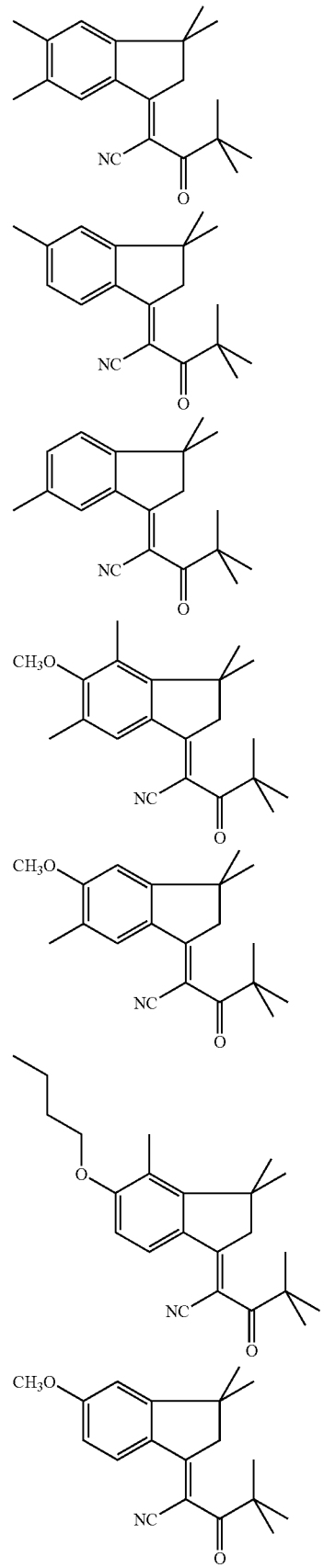

-continued

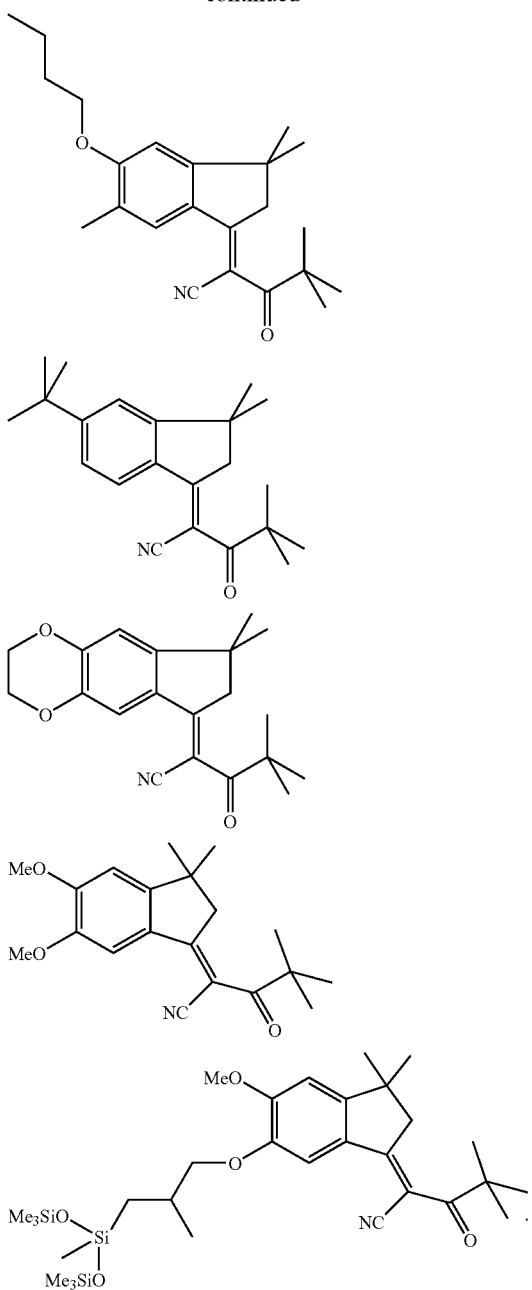

15. The cosmetic composition according to claim 14, wherein said indanylidene compounds are UV absorbers and protect the skin and/or the hair against UV radiation.

16. The cosmetic composition according to claim 14, wherein said composition further comprises at least one tanning agent and/or artificial self-tanning agent for the skin.

17. The cosmetic composition according to claim 14, wherein said composition further comprises one or more further UV absorbers.

18. The cosmetic composition according to claim 14, wherein said composition further comprises one or more other UV absorbers selected from the group consisting of ethylhexylmethoxy cinnamate, 2-ethylhexyl-2-cyano-3,3-diphenyl acrylate, 2-phenylbenzimidazolesulphonic acid, methylbenzylidene campher, 4-t-butyl-4'-methoxy-dibenzoylmethane, phenylene-bis-benzimidazyl-tetrasulphonic acid disodium salt, terephthadylidene-dibornanesulphonic acid and salts thereof, phenol, 2-(2H -benzotriazol-2-yl)-4-methyl-6-(2-methyl-3(1,3,3,3-tetramethyl-1(trimethylsilyl)-oxy) -disiloxyanyl)-propyl), benzylidene malonate polysiloxane, 2,2'-methylene-bis-(6-(2H -benzotriazol-2-yl)-4-1,1,3,3-tetrmethylbutyl)-phenol), 2,4-bis[{(4-(2-ethylhexyloxy-2-hydroxy}-phenyl]-6-(4-methoxyphenyl)-1,3,5-triazine, 4,4',4-(1,3,5-triazine-2,4,6-triyltriimino)-tris-benzoic acid tris(2-ethylhexyl ester), 4,4'-[(6[4-(1,1-dimethyl) -aminocarbonyl)-phenylamino]-1,3,5-triazine-2, 4-diyl)diimino]-bis-(benzoic acid-2-ethylhexyl ester), zinc oxide and titanium dioxide.

19. The cosmetic composition according to claim 14, wherein said composition further comprises UV absorbers and additionally coated or noncoated pigments or nanopigments of metal oxides.

20. The cosmetic composition according to claim 14, wherein said composition further comprises UV absorbers and additionally finely divided pigments such that a UV broad-band protection performance with a critical wavelength $\lambda_{crit}>380$ nm results therefrom.

21. A cosmetic composition for protecting skin and hair, comprising the indanylidene compound selected from the group consisting of 2-(5-methoxy-3,3,4,6-tetramethyl-1-indanylidene)-4,4-dimethyl-3-oxo-pentanonitrile, 2-(3,3,5,6-tetramethyl-1-indanylidene)-4,4-dimethyl-3-oxo-pentanonitrile 2-(3,3,6-trimethyl-1-indanylidene)-4,4-dimethyl-3-oxo-pentanonitrile, 2-(5,6-ethylenedioxo-3,3-dimethyl-1-indanylidene)-4,4-dimethyl-3-oxo-pentanonitrile, 2-(5-methoxy-3,3,6-trimethyl-1-indanylidene)-4,4-dimethyl-3-oxo-pentanonitrile, 2-(5-methyl-3,3-dimethyl-1-indanylidene)-4,4-dimethyl -3-oxo-pentanonitrile, 2-(5-methoxy-3,3-dimethyl-1-indanylidene)-4,4-dimethyl-3-oxo-pentanonitrile, 2-(5-t-butyl-3,3-dimethyl-1-indanylidene)-4,4-dimethyl-3-oxo -pentanonitrile, 2-(5-n-butoxy-3,3,4-trimethyl-1-indanylidene)-4,4-dimethyl-3-oxo-pentanonitrile, 2-(5-n-butoxy-3,3,6-trimethyl-1-indanylidene)-4,4-dimethyl-3-oxo -pentanonitrile, 2-[(5-methoxy-3,3-dimethyl-(2-methyl-3-(1,3,3,3-tetramethyl-1-(trimethyl-silyloxy)-disiloxanyl)-propyl)-indanylidene)]-4, 4dimethyl-3-oxo-pentanonitrile, 2-(5,6-dimethoxy-3,3-dimethyl-1-indanylidene)-4,4-dimethyl-3-oxo-pentanonitrile, and 2-(6-acetoxy-3,3-dimethyl-5-methoxy-1-indanylidene4,4-dimethyl-3-oxo-pentanonitrile.

* * * * *